US008940930B2

(12) United States Patent  
Batra et al.

(10) Patent No.: US 8,940,930 B2  
(45) Date of Patent: *Jan. 27, 2015

(54) TREPROSTINIL PRODUCTION

(75) Inventors: Hitesh Batra, Herndon, VA (US); Raju Penmasta, Ashburn, VA (US); Vijay Sharma, Olney, MD (US); Sudersan M. Tuladhar, Silver Spring, MD (US); David A. Walsh, Spotsylvania, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 323 days.

This patent is subject to a terminal disclaimer.

(21) Appl. No.: 13/435,708

(22) Filed: Mar. 30, 2012

(65) Prior Publication Data

US 2012/0190888 A1 Jul. 26, 2012

Related U.S. Application Data

(63) Continuation of application No. 13/151,465, filed on Jun. 2, 2011.

(60) Provisional application No. 61/351,115, filed on Jun. 3, 2010.

(51) Int. Cl.
```
C07C 51/353    (2006.01)
C07C 59/72     (2006.01)
C07C 51/09     (2006.01)
C07C 51/367    (2006.01)
C07C 67/343    (2006.01)
C07C 253/30    (2006.01)
C07F 7/18      (2006.01)
```

(52) U.S. Cl.
CPC ............ *C07C 59/72* (2013.01); *C07C 51/09* (2013.01); *C07C 51/367* (2013.01); *C07C 67/343* (2013.01); *C07C 253/30* (2013.01); *C07F 7/1892* (2013.01); *C07B 2200/07* (2013.01)
USPC ....................................................... 562/466

(58) Field of Classification Search
USPC ....................................................... 562/466
See application file for complete search history.

(56) References Cited

U.S. PATENT DOCUMENTS

| 4,306,075 A | 12/1981 | Aristoff |
| 4,306,076 A | 12/1981 | Nelson |
| 4,424,376 A | 1/1984 | Moniot et al. |
| 4,463,183 A | 7/1984 | Haslanger |
| 4,486,598 A | 12/1984 | Aristoff |
| 4,544,764 A | 10/1985 | Aristoff |
| 4,668,814 A | 5/1987 | Aristoff |
| 4,683,330 A | 7/1987 | Aristoff |
| 5,039,814 A | 8/1991 | Shuman et al. |
| 5,153,222 A | 10/1992 | Tadepalli et al. |
| 6,054,486 A | 4/2000 | Crow et al. |
| 6,441,245 B1 | 8/2002 | Moriarty et al. |
| 6,521,212 B1 | 2/2003 | Cloutier et al. |
| 6,528,688 B2 | 3/2003 | Moriarty et al. |
| 6,700,025 B2 | 3/2004 | Moriarty et al. |
| 6,756,033 B2 | 6/2004 | Cloutier et al. |
| 6,765,117 B2 | 7/2004 | Moriarty et al. |
| 6,803,386 B2 | 10/2004 | Shorr et al. |
| 6,809,223 B2 | 10/2004 | Moriarty et al. |
| 6,933,385 B2 * | 8/2005 | Westermann et al. ........ 544/106 |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 7,879,909 B2 | 2/2011 | Wade et al. |
| 7,999,007 B2 | 8/2011 | Jeffs et al. |
| 8,481,782 B2 * | 7/2013 | Batra et al. ..................... 562/466 |
| 2002/0173672 A1 | 11/2002 | Moriarty et al. |
| 2004/0176645 A1 | 9/2004 | Moriarty et al. |
| 2005/0085540 A1 | 4/2005 | Phares et al. |
| 2005/0101608 A1 | 5/2005 | Santel |
| 2005/0165111 A1 | 7/2005 | Wade et al. |
| 2005/0282901 A1 | 12/2005 | Phares et al. |
| 2005/0282903 A1 | 12/2005 | Wade et al. |
| 2007/0078095 A1 | 4/2007 | Phares et al. |
| 2007/0078182 A1 | 4/2007 | Phares et al. |
| 2007/0082948 A1 | 4/2007 | Phares et al. |
| 2008/0200449 A1 | 8/2008 | Olschewski et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0124697 A1 | 5/2009 | Cloutier et al. |
| 2009/0163738 A1 | 6/2009 | Batra et al. |
| 2009/0281189 A1 | 11/2009 | Walsh |
| 2010/0076083 A1 | 3/2010 | Olschewski |
| 2010/0282622 A1 | 11/2010 | Phares |
| 2011/0092599 A1 | 4/2011 | Wade et al. |
| 2011/0118213 A1 | 5/2011 | Phares et al. |
| 2011/0144204 A1 | 6/2011 | Jeffs et al. |
| 2011/0224236 A1 | 9/2011 | Rothblatt et al. |
| 2011/0319641 A1 * | 12/2011 | Batra et al. ..................... 549/423 |
| 2012/0004307 A1 | 1/2012 | Wade et al. |
| 2012/0010159 A1 | 1/2012 | Rothblatt et al. |
| 2012/0197041 A1 * | 8/2012 | Batra et al. ..................... 562/466 |

FOREIGN PATENT DOCUMENTS

| CA | 2 710 726 A1 | 1/2012 |
| CN | 101891596 A | 11/2010 |

(Continued)

OTHER PUBLICATIONS

Alexander et al., "The Synthesis of Benzindene Prostacyclin Analogs as Potential Antiulcer Agents," Prostaglandins, 1986, 32(5):647-653.

(Continued)

*Primary Examiner* — Rosalynd Keys
(74) *Attorney, Agent, or Firm* — Foley & Lardner LLP

(57) ABSTRACT

The present invention is directed to a novel method for preparing a synthetic intermediates for treprostinil. Also described are methods of preparing treprostinil comprising utilizing novel intermediates described herein as well as novel intermediates useful for synthesis prostacyclin derivatives, such as treprostinil.

9 Claims, No Drawings

(56) References Cited

FOREIGN PATENT DOCUMENTS

| CN | 101891715 A | 11/2010 |
|---|---|---|
| EP | 0 004 335 A2 | 10/1979 |
| EP | 0 087 237 B1 | 5/1986 |
| EP | 0 175 450 B1 | 3/1989 |
| EP | 0 159 784 B1 | 6/1989 |
| EP | 0 496 548 A1 | 7/1992 |
| WO | WO 98/39337 A1 | 9/1998 |
| WO | WO 99/21830 A1 | 5/1999 |
| WO | WO 03/070163 A2 | 8/2003 |
| WO | WO 2005/007081 A2 | 1/2005 |
| WO | WO 2007/134292 A2 | 11/2007 |
| WO | WO 2008/100977 A2 | 8/2008 |
| WO | 2009/117095 A1 | 9/2009 |
| WO | WO 2012/009816 A1 | 1/2012 |

OTHER PUBLICATIONS

U.S. Appl. No. 13/160,034, filed Jun. 14, 2011, Wade et al.
Aristoff et al., "Synthesis and Structure-Activity Relationship of Novel Stable Prostacyclin Analogs," Advances in Prostaglandin, Thromboxane, and Leukotriene Research, Samuelsson et al., .Eds., 1983, 11:267-274.
Aristoff et al., "Synthesis of Benzopyran Prostaglandins, Potent Stable Prostacyclin Analogs, Via an Intramolecular Mistunobu Reaction," Tetrahedron Letters, 1984, 25(36):3955-3958.
Aristoff et al., "Total Synthesis of a Novel Antiulcer Agent via a Modification of the Intramolecular Wadsworth-Emons-Wittig Reaction," J. Am. Chem. Soc., 1985, 107:7967-7974.
Batra et al., "Crystallization Process Development for a Stable Polymorph of Treprostinil Diethanolamine (UT-15C) by Seeding," Organic Process Research & Development, 2009, 13:242-249.
Belch et al., "Randomized, Double-Blind, Placebo-Controlled Study Evaluating the Efficacy and Safety of AS-013, a Prostaglandin E1 Prodrug, in Patients with Intermittent Claudication," Circulation, May 6, 1997, 95(9):2298-2302.
Chemburkar et al., "Dealing with the Impact of Ritonavir Polymorphs on the Late Stages of Bulk Drug Process Development," Organic Process Research & Development, 2000, 4:413-417.
Chung et al., "Promoters for the (Alkyne)hexacarbonyldicobalt-Based Cyclopentenone Synthesis," Organometallics, 1993, 12:220-223.
Clark et al., "High-Performance Liquid Chromatographic Method for Determining the Enantiomeric Purity of a Benzindene Prostaglandin by a Diastereomeric Separation," Journal of Chromatography, 1987, 408:275-283.
Hardinger et al., "Triply-Convergent Syntheses of Two Homochiral Arene-Fused Prostacyclin Analogs Related to U68,215," Bioorganic & Medicinal Chemistry Letters, 1991, 1(1):79-82.
Hicks et al., "A Practical Titanium-Catalyzed Synthesis of Bicyclic Cyclopentenones and Allylic Amines," J. Org. Chem., 1996, 61:2713-2718.
Jeong et al., "Catalytic Version of the Intramolecular Pauson-Khand Reaction," J. Am. Chem. Soc., 1994, 116:3159-3160.
Khand et al., "Organocobalt Complexes. Part II. Reaction of Acetylenehexacarbonyl-dicobalt Complexes, $(R^1C_2R^2)Co_2(CO)_6$, with Norbornene and its Derivatives," J. Chem. Soc., J.C.S. Perkin I., 1973, 977-981.
Mathre et al., "A Practical Enantioselective Synthesis of α,α-Diaryl-2-pyrrolidinemethanol. Preparation and Chemistry of the Corresponding Oxazaborolidines," J. Org. Chem., 1991, 56:751-762.
Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.

Mullin, John W., "Crystallization and Precipitation," Ullmann's Encyclopedia of Industrial Chemistry, 2002, 1-51.
Mulzer et al., "Asymmetric Synthesis of Carbacyclin Precursors by Pauson-Khand Cyclization," Liebigs Ann. Chem., 1988, 891-897.
Nelson, Norman A., "Prostaglandin Nomenclature," J. Med. Chem., Sep. 1974, 17(9):911-918.
Pagenkopf et al., "Photochemical Promotion of the Intramolecular Pauson-Khand Reaction. A New Experimental Protocol for Cobalt-Catalyzed [2+2+1] Cycloadditons," J. Am. Chem. Soc., 1996, 118:2285-2286.
Pagenkopf, Brian L., "Substrate and Reagent Control of Diastereoselectivity in Transition Metal-Mediated Process: Development of a Catalytic Photo Promoted Pauson-Khand Reaction," Diss. Abstr. Int., 57(12):7535, 1977, Abstract.
Paulson, Peter L., "The Khand Reaction," Tetrahedron, 1985, 41(24):5855-5860.
Schore, Neil E., "Transition-Metal-Mediated Cycloaddition Reactions of Alkynes in Organic Synthesis," Chem. Rev., 1988, 88:1081-1119.
Shambayati et al., "N-Oxide Promjoted Pauson-Khand Cyclizations at Room Temperature," Tetrahedron Letters, 1990, 31(37):5289-5292.
Snell et al., "Investigating the Effect of Impurities on Macromolecule Crystal Growth in Microgravity," Crystal Growth & Design, 2001, 1(2):151-158.
Sorbera et al. "UT-15. Treatment of Pulmonary Hypertension Treatment of Peripheral Vascular Disease," Drug of the Future, 2001, 26(4), 364-374.
Takano et al., "Enantiodivergent Synthesis of Both Enantiomers of Sulcatol and Matsutake Alcohol from (R)-Epichlorohydrin," Chemistry Letters, 1987, 2017-2020.
Viedma, Cristobal, "Selective Chiral Symmetry Breaking during Crystallization: Parity Violation of Cryptochiral Environment in Control?" Crystal Growth & Design, 2007,7(3):553-556.
Zhang et al., "A Nickel(0)-Catalyzed Process for the Transformation of Enynes to Bicyclic Cyclopentenones," J. Org. Chem., 1996, 61:4498-4499.
Defendant Sandoz Inc.'s Invalidity Contentions, filed Sep. 7, 2012, in *United Therapeutics Corporation v. Sandoz, Inc.*, Civil Action No. 12-1617 (PGS)(LHG), 102 pages.
Corey et al. "Novel Electronic Effects of Remote Substituents on the Oxazaborolidine-Catalyzed Enantioselective Reduction of Ketones," Tetrahedron Letters, 1995, 36(50):9153-9156.
Greene et al., "Protecting Groups," Protective Groups in Organic Synthesis, 2d. Ed., 1991, p. 1-11.
Rowley et al., "Application of the Pauson-Khand reaction to the synthesis of pentalenic acid," Journal of Organometallic Chemistry, 1991, 413:C5-C9.
U.S. Appl. No. 13/409,685, filed Mar. 1, 2012, Sharma, Vijay.
Comins et al., "Ortho Metalation Directed by α-Amino Alkoxides," J. Org. Chem., 1984, 49:1078-1083.
Comins et al., "Ortho Substitution of M-Anisaldehyde via α-Amino Alkoxide Directed Lithiation," J. Org. Chem., 1989, 54:3730-3732.
Pansegrau et al., "The Oxazoline-Benzyne Route to 1,2,3-Trisubstituted Benzenes. Tandem Addition of Organolithiums, Organocuprates, and α-Lithionitriles to Benzynes," J. Am. Chem. Soc., 1988, 110:7178-7184.
Patterson et al., "Acute Hemodynamic Effects of the Prostacyclin Analog 15AU81 in Severe Congestive Heart Failure," Am. J. Cardio., 1995, 75:26A-33A.
Whittle et al., "Antithrombotic Assessment and Clinical Potential of Prostacyclin Analogues," Progress in Medicinal Chemistry, Ellis et al. Eds., 1984, Chapter 6, vol. 21, 238-279.

\* cited by examiner

TREPROSTINIL PRODUCTION

The present application is a Continuation of U.S. application Ser. No. 13/151,465, filed Jun. 2, 2011, which claims the benefit of U.S. provisional application No. 61/351,115 filed Jun. 3, 2010, which are incorporated herein by reference in their entirety.

The present application relates to a process for producing prostacyclin derivatives, such as Treprostinil, and novel intermediate compounds useful in the process.

(+)-Treprostinil (also known as UT-15) is the active ingredient in Remodulin®, a commercial drug approved by FDA for the treatment of pulmonary arterial hypertension (PAH). It was first described in U.S. Pat. No. 4,306,075. Treprostinil is a stable analog of prostacyclin (PGI$_2$) belonging to a class of compounds known as benzindene prostacyclins, which are useful pharmaceutical compounds possessing activities such as platelet aggregation inhibition, gastric secretion reduction, lesion inhibition, and bronchodilation.

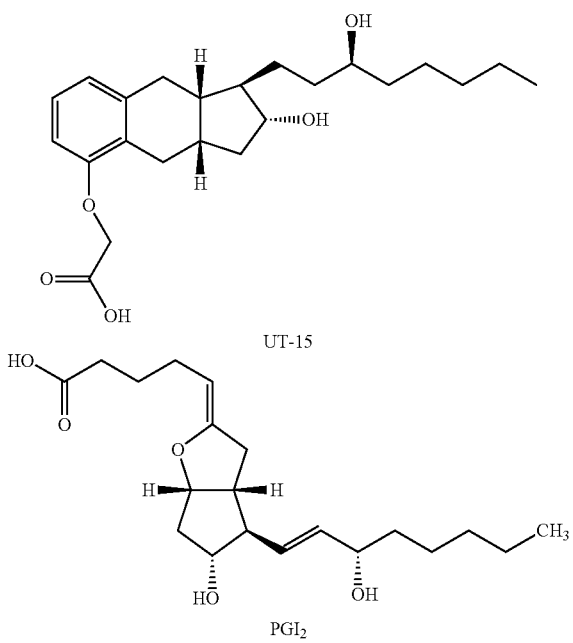

U.S. Pat. No. 5,153,222 describes use of treprostinil for treatment of pulmonary hypertension. Treprostinil is approved for the intravenous as well as subcutaneous route, the latter avoiding potential septic events associated with continuous intravenous catheters. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,803,386 discloses administration of treprostinil for treating cancer such lung, liver, brain, pancreatic, kidney, prostate, breast, colon and head-neck cancer. U.S. patent application publication No. 2005/0165111 discloses treprostinil treatment of ischemic lesions. U.S. Pat. No. 7,199,157 discloses that treprostinil treatment improves kidney functions. U.S. Pat. No. 7,879,909 discloses treprostinil treatment of neuropathic foot ulcers. U.S. publication No. 2008/0280986 discloses treprostinil treatment of pulmonary fibrosis, interstitial lung disease with treprostinil and asthma. U.S. Pat. No. 6,054,486 discloses treatment of peripheral vascular disease with treprostinil. U.S. patent application publication No. 2009/0036465 discloses combination therapies comprising treprostinil. U.S. publication No. 2008/0200449 discloses delivery of treprostinil using a metered dose inhaler. U.S. Pat. Nos. 7,417,070, 7,384,978 and 7,544,713 as well as U.S. publications Nos. 2007/0078095, 2005/0282901, and 2008/0249167 describe oral formulations of treprostinil and other prostacyclin analogs as well as their use for treatment of a variety of conditions. U.S. provisional application No. 61/354,949 filed Jun. 15, 2010 discloses the use of orally administered treprostinil for treatment of Raynaud's phenomenon, systemic sclerosis and digital ischemic lesions.

Treprostinil and other prostacyclin derivatives have been prepared as described in Moriarty, et al in *J. Org. Chem.* 2004, 69, 1890-1902, *Drug of the Future*, 2001, 26(4), 364-374, U.S. Pat. Nos. 4,306,075, 6,441,245, 6,528,688, 6,700,025, 6,765,117, 6,809,223 and US Publication No. 2009/0163738. The entire teaching of these documents are incorporated herein by reference in their entirety. The methods described in these patent documents, however, do not describe a feasible production method for producing stereochemically pure treprostinil because, for example, the methods require the use of expensive reagents and tedious chromatographic purification techniques. Therefore, there is a need in the art for an economical, efficient and simplified method for preparing treprostinil and its synthetic intermediates.

SUMMARY

One embodiment relates to a method of preparing a synthetic intermediate of treprostinil represented by the following structural formula:

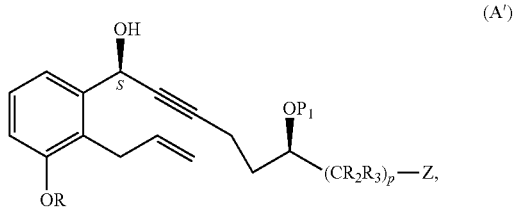

wherein:
R is —(CH$_2$)$_n$X or P$_1$;
X is H, phenyl, —CN, —OR$_1$ or COOR$_1$;
R$_1$ is an alkyl, THP or TBDMS;
P$_1$, for each occurrence, is independently an alcohol protecting group;
R$_2$ and R$_3$ are each independently —H or an alkyl;
Z is —H, cycloalkyl or phenoxy (i.e. —O-phenyl);
n is 0, 1, 2 or 3; and
p is 1, 2, 3, 4 or 5.

The method comprises the step of reacting an aldehyde compound represented by structural formula (I):

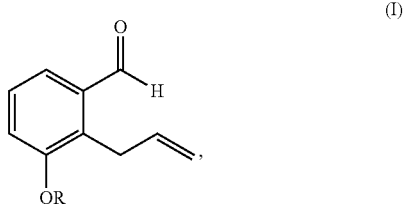

with an alkyne compound represented by structural formula (a):

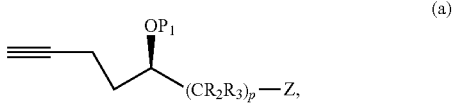

wherein R, P$_1$, R$_1$, R$_2$, R$_3$, X, Z, n and p are as described above for structural formula (A).

Another embodiment is directed to a method of preparing a prostacyclin derivative (e.g., treprostinil) comprising reaction 1, and optionally comprising one or more reaction steps 2-9 according to Scheme 2.

Yet another embodiment relates to a method of preparing a synthetic intermediate of treprostinil represented by the following structural formula:

(A)

wherein:
$P_1$ is an alcohol protecting group;
R is —$(CH_2)_nX$;
X is H, phenyl, —CN, —$OR_1$ or $COOR_1$;
$R_1$ is an alkyl, THP or TBDMS; and
n is 1, 2 or 3.

The method comprises reacting a compound represented by structural formula (I):

(I)

with a compound represented by structural formula (a):

(a)

wherein R and $P_1$ are as described above for structural formula (A).

Another embodiment is to a method of preparing treprostinil comprising reaction 1, and optionally comprising one or more reactions 2-9 according to Scheme 2.

Yet another embodiment is a compound of formula (1):

(1)

wherein:
R is $(CH_2)_mCO_2R_1$,
m is 1, 2 or 3, and
$R_1$ is an alkyl group, THP, TBDMS or a substituted or unsubstituted benzyl group.

And yet another embodiment is a compound represented by structural formula (A):

(A)

wherein:
$P_1$ is an alcohol protecting group;
wherein R is $(CH_2)_mCO_2R_1$, m is 1, 2 or 3, and
$R_1$ is an alkyl group or a substituted or unsubstituted benzyl group.

And yet another embodiment is a compound represented by structural formula (4):

(4)

wherein:
each of $P_1$ and $P_2$ is an alcohol protecting group;
wherein R is $(CH_2)_mCO_2R_1$, m is 1, 2 or 3, and
$R_1$ is an alkyl group, or a substituted or unsubstituted benzyl group.

And yet another embodiment is a compound represented by structural formula (5):

(5)

wherein:
each of $P_1$ and $P_2$ is an alcohol protecting group;
wherein R is $(CH_2)_mCO_2R_1$, m is 1, 2 or 3, and
$R_1$ is an alkyl group, or a substituted or unsubstituted benzyl group.

And yet another embodiment is a compound represented by structural formula (6):

(6)

wherein:
P₁ is an alcohol protecting group;
wherein m is 1, 2 or 3, and
R₁ is an alkyl group, or hydrogen.

DETAILED DESCRIPTION

Unless otherwise specified, "a" or "an" means "one or more".

The present application is directed to methods of preparing treprostinil and synthetic intermediates useful of synthesizing treprostinil as well to synthetic intermediates themselves. The present application is also directed to methods of preparing treprostinil or a pharmaceutically acceptable salt thereof comprising the alkyne addition reaction described herein. Preferred treprostinil salts may include the sodium salt and the diethanolamine salt (see, e.g., U.S. Pat. No. 7,417,070).

In some embodiments, the present application is directed to a method of preparing a synthetic intermediate (A) of treprostinil through a stereoselective alkyne addition reaction.

One embodiment is directed to a novel method (reaction 1) for preparing a compound of structural formula (A) comprising the step of reacting an aldehyde of structural formula (I) with an alkyne of structural formula (a):

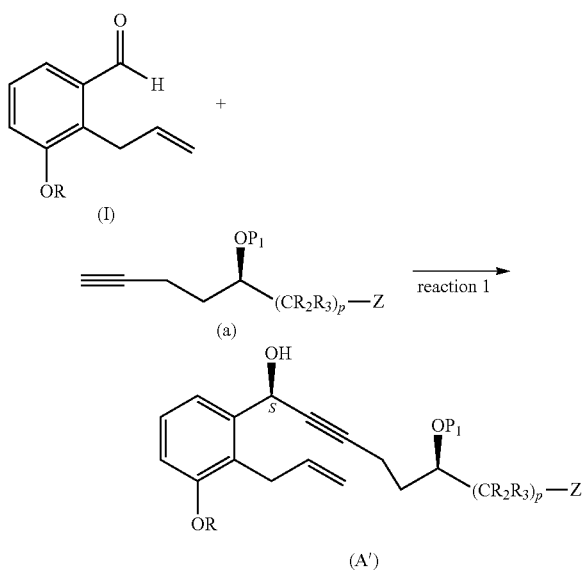

wherein R, P₁, R₁, R₂, R₃, X, Z, n and p are as described above for structural formula (A').

Another embodiment is directed to a novel method (reaction 1) for preparing a compound of structural formula (A) comprising the step of reacting an aldehyde of structural formula (I) with an alkyne of structural formula (a):

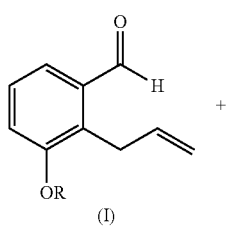

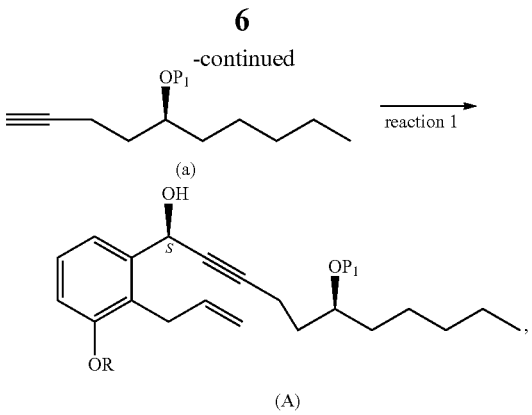

wherein:
P₁ is an alcohol protecting group;
R is —(CH₂)ₙX;
X is H, phenyl, —CN, —OR₁ or COOR₁;
R₁ is an alkyl, THP, TBDMS or a substituted or unsubstituted benzyl group; and n is 1, 2 or 3.

As used herein, "an alcohol protecting group" is a functional group that protects the alcohol group from participating in reactions that are occurring in other parts of the molecule. Suitable alcohol protecting groups are well known to those of ordinary skill in the art and include those found in T. W. Greene, *Protecting Groups in Organic Synthesis*, John Wiley & Sons, Inc. 1981, the entire teachings of which are incorporated herein by reference. Exemplary alcohol protecting groups include, but are not limited to, actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS ether), tetrahydropyranyl (THP), methyl ether and ethoxyethyl ether (EE).

An alkyl group may be a saturated straight-chain or branched aliphatic group. For example, an alkyl group may a (C1-C6)alkyl, (C1-C5)alkyl, (C1-C4)alkyl or (C1-C3)alkyl. Examples of alkyl groups include methyl, ethyl, n-propyl, isopropyl, n-butyl, isobutyl, sec-butyl, tert-butyl, pentyl, isoamyl, and hexyl. An alkyl group is optionally substituted with an alkyl, a cycloalkyl (e.g., cyclopentyl or cyclohexyl), an aryl (e.g., phenyl), or heteroaryl group.

A phenyl group may be optionally substituted with one or more substituents, which may be independently selected from the group consisting of —NO₂, —CN, halogen (e.g., —F, —Cl, —Br or —I), (C1-C3)alkyl, halo(C1-C3)alkyl, (C1-C3)alkoxy and halo(C1-C3)alkoxy.

A substituted benzyl group may be optionally substituted at one or more meta, ortho or para positions with one or more substituents, which may be independently selected from the group consisting of —NO₂, —CN, halogen (e.g., —F, —Cl, —Br or —I), (C1-C3)alkyl, halo(C1-C3)alkyl, (C1-C3) alkoxy and halo(C1-C3)alkoxy.

Values and particular values for the variables depicted in reaction 1 are provided in the following paragraphs:

P₁ is an alcohol protecting group. In one embodiment, P₁ is THP or TBDMS. Alternatively, P₁ is THP.

R is —(CH₂)ₙX or P₁. In one embodiment, R is selected from the group consisting of methyl, benzyl, —CH₂COOMe, —CH₂COOCH₂Ph, THP and TBDMS. Alternatively, R is methyl.

X is —H, phenyl, —CN, —OR₁ or COOR₁. In one embodiment, X is —H. In another embodiment, X is an optionally substituted phenyl. Alternatively, X is unsubstituted phenyl. In one embodiment, when n is 0, X is not —CN, —OR₁ or COOR₁.

R₁ is an alkyl, THP or TBDMS. In one embodiment, R₁ is a (C1-C3)alkyl. Alternatively, R₁ is methyl. In another alternative, R₁ is benzyl.

n is 0, 1, 2 or 3. In one embodiment, n is 1. Alternatively, n is 0.

R₂ and R₃ are each independently —H or an alkyl. In one embodiment, R₂ and R₃ are both —H. In another embodiment, R₂ and R₃ are each independently —H or a (C1-C3) alkyl. Alternatively, R₂ and R₃ are both methyl. In another alternative, R₂ is —H and R₃ is methyl.

Z is —H, cycloalkyl or phenoxy. In one embodiment, Z is —H. Alternatively, Z is a (C3-C6)cycloalkyl. In another alternative, Z is

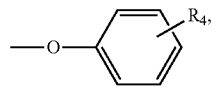

wherein R₄ is —H, —Cl, —Br, —F, —I, halo(C1-C3)alkyl, (C1-C3)alkyl, or —O—(C1-C3)alkyl. In one embodiment, R₄ is R₄ is —H, —Cl, —Br, —F, —I, —CF₃, -Me or —OMe.

p is 1, 2, 3, 4 or 5. In one embodiment, p is 5. In another embodiment, p is 1.

P₂ is an alcohol protecting group. In one embodiment, P₂ is THP or TBDMS. Alternatively, P₂ is TBDMS.

In one embodiment, the alkyne of structural formula (a) is selected from the following:

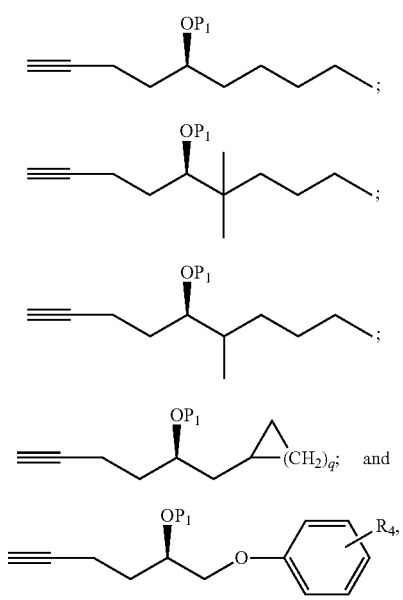

wherein: q is 1, 2, 3 or 4; and R₄ is as described above.

In one embodiment, for reaction 1 described above, P₁ may be THP.

In another embodiment, R may be selected from the group consisting of methyl, benzyl, —CH₂COOMe, —CH₂COOCH₂Ph, THP and TBDMS. Alternatively, R is methyl.

In yet another embodiment, R is methyl and P₁ is THP.

In yet another embodiments, R is —CH₂CO₂R₁, wherein R₁ is an alkyl group, such as a straight or branched C1-C5 alkyl group, or a substituted or unsubstituted benzyl group, and P₁ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).

When reaction 1 is carried out in the presence of a chiral inducing agent, the reaction may yield a product having predominantly S configuration of the hydroxyl group at the benzylic carbon position. A "chiral inducing agent" is a compound that is used to create stereoselectivity at a chiral center. For example, (+)—N-methylephiderine may be used as the chiral inducing agent for reaction 1 described above. In one embodiment, at least 70%, 80%, 90%, 95%, 97%, 98%, 99%, 99.5%, 99.9% or 100% by weight of the product of reaction 1 is represented by structural formula (A), i.e., the compound prepared by reaction 1 has at least 40%, 60%, 80%, 90%, 94%, 96%, 98%, 99.0%, 99.8% or 100% chiral purity.

The compound of structural formula (A) can be subsequently converted to a prostacyclin derivative such as treprostinil according to Scheme 2, reaction steps 2-9.

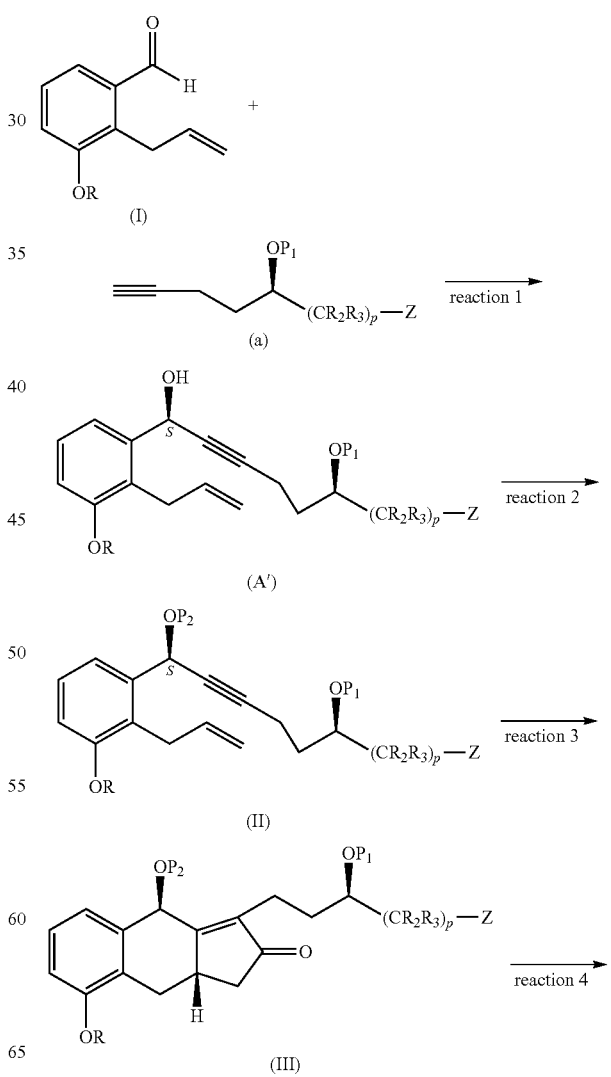

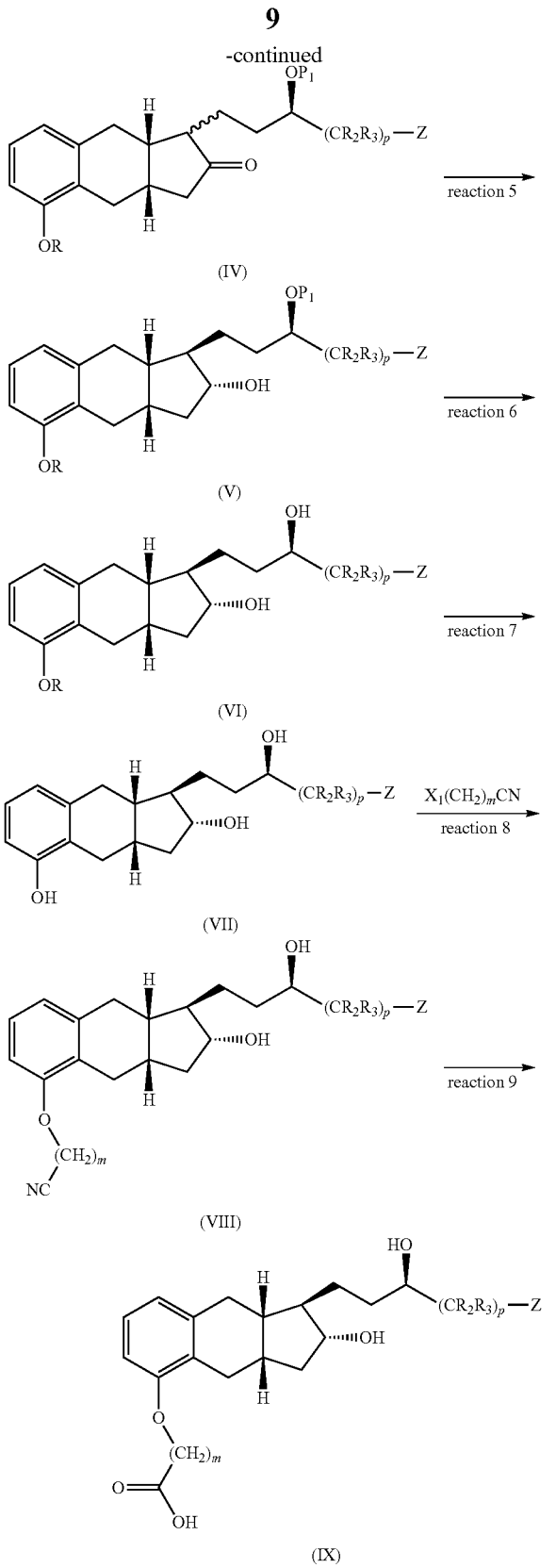

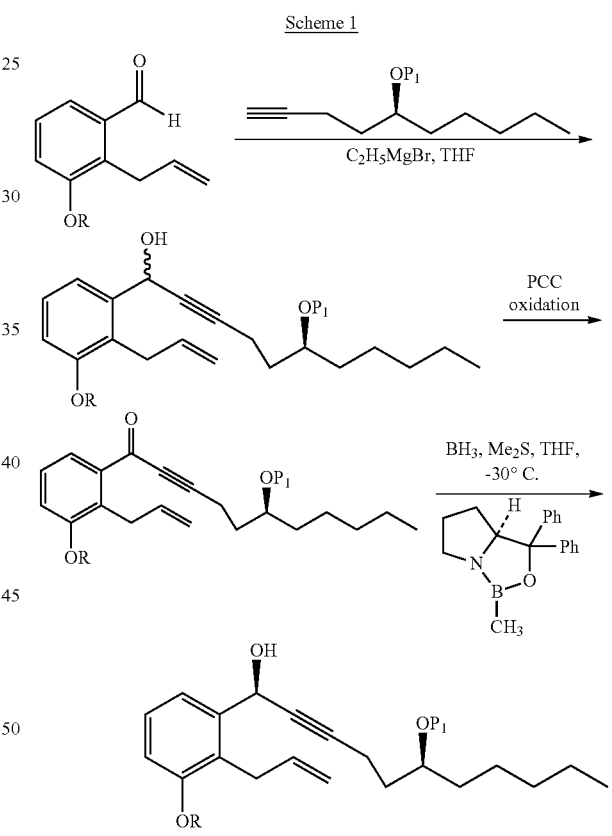

In Scheme 2', values and particular values for R, $R_2$, $R_3$, p, Z and $P_1$ are as described above for structural formula (A'); $P_2$ is an alcohol protecting group (e.g., TBDMS); and m is 1, 2, or 3.

In some embodiments, reaction 1 may be carried out in the presence of a base and a zinc reagent. An exemplary zinc reagent includes zinc triflate ($Zn(OTf)_2$). Suitable bases that may be used include, for example, an alkali carbonate, an alkali hydroxide, an amine and an ammonium hydroxide. In some embodiments, $Et_3N$ may be preferred as the base.

In some embodiments, reaction 1 as described in any one of the foregoing embodiments may be carried out in an organic solvent. Suitable organic solvents include, for example, ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile. In one specific embodiment, reaction 1 may be carried out in toluene.

U.S. Pat. Nos. 6,700,025, 6,809,223, 6,528,668 and 6,441,245 describe a method, which may be used for preparing some of the compounds of structural formula (A). This method, depicted in Scheme 1, however, includes 3 reaction steps.

Compared to the prior art method, reaction 1 of the present invention may have one or more of the following advantages: (1) reaction 1 has high diastereoselectivity, wherein the product with greater than 95% chiral purity can be obtained. (2) the prior method requires 3-step synthesis; whereas the method (reaction 1) of the present invention only has a single step, which shortens the number of chemical steps needed; eliminates the tedious column chromatographic purifications involved in the extra two steps and saves manpower and large volume of solvents. (3) reaction 1 may be carried out at room temperature, and therefore no cryogenic reactors are needed; (4) reaction 1 is less expensive than the prior art method as the prior art method involves the use of expensive reagents as needed in the Corey asymmetric reduction. (5) reaction 1 is an eco-friendly method as it does not require the use of obnoxious borane-dimethyl sufide complex in the Corey asymmetric reduction.

In some embodiments, the compound of structural formula (A) may be subsequently converted to a prostacyclin derivative such as treprostinil according to Scheme 2, reaction steps 2-9.

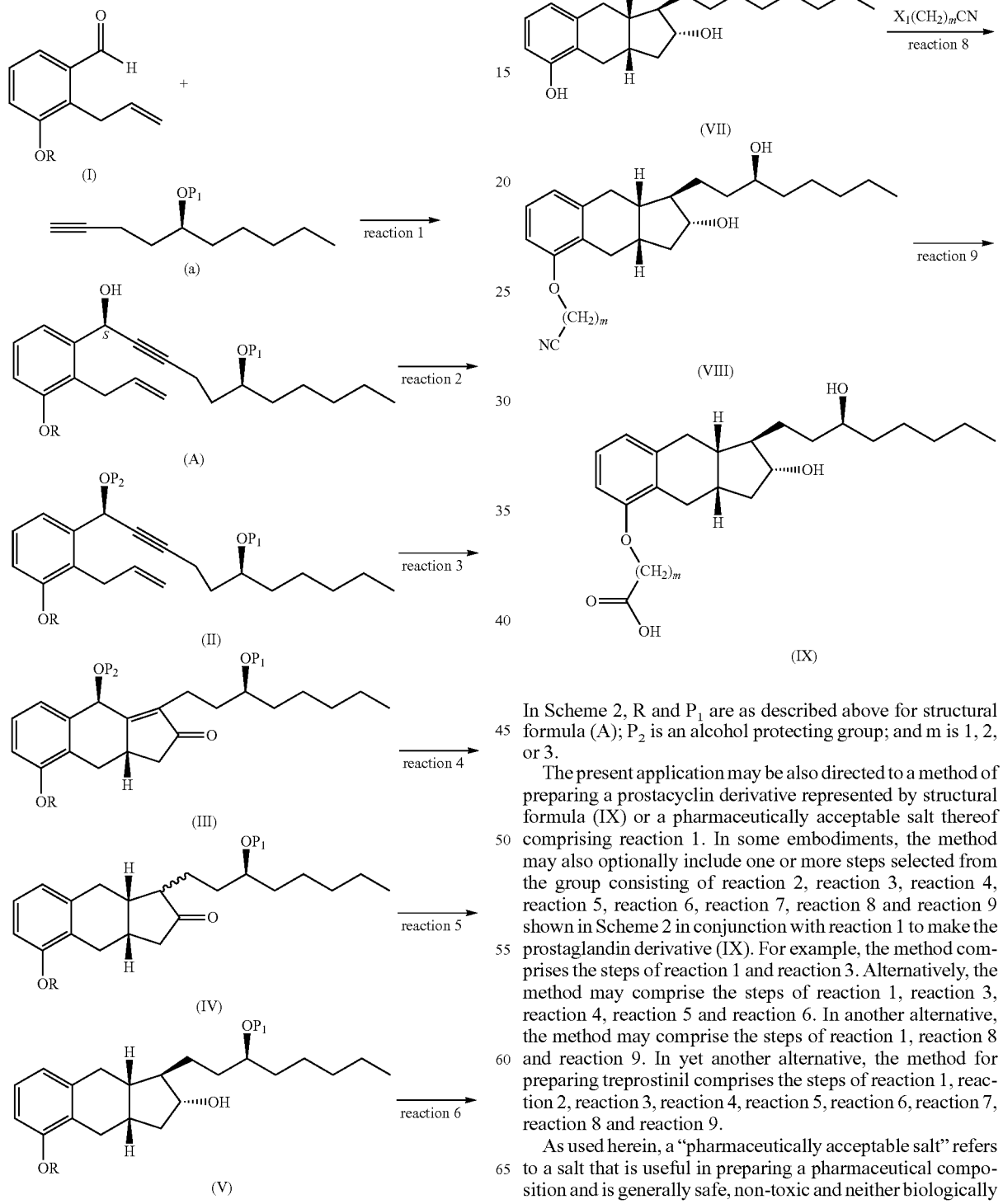

In Scheme 2, R and $P_1$ are as described above for structural formula (A); $P_2$ is an alcohol protecting group; and m is 1, 2, or 3.

The present application may be also directed to a method of preparing a prostacyclin derivative represented by structural formula (IX) or a pharmaceutically acceptable salt thereof comprising reaction 1. In some embodiments, the method may also optionally include one or more steps selected from the group consisting of reaction 2, reaction 3, reaction 4, reaction 5, reaction 6, reaction 7, reaction 8 and reaction 9 shown in Scheme 2 in conjunction with reaction 1 to make the prostaglandin derivative (IX). For example, the method comprises the steps of reaction 1 and reaction 3. Alternatively, the method may comprise the steps of reaction 1, reaction 3, reaction 4, reaction 5 and reaction 6. In another alternative, the method may comprise the steps of reaction 1, reaction 8 and reaction 9. In yet another alternative, the method for preparing treprostinil comprises the steps of reaction 1, reaction 2, reaction 3, reaction 4, reaction 5, reaction 6, reaction 7, reaction 8 and reaction 9.

As used herein, a "pharmaceutically acceptable salt" refers to a salt that is useful in preparing a pharmaceutical composition and is generally safe, non-toxic and neither biologically nor otherwise undesirable pharmaceutical use.

Compounds with basic groups, such as amine groups, can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. A particularly preferred salt is the diethanolamine salt of treprostinil.

In one embodiment, the prostacyclin derivative (e.g., treprostinil) prepared according to the methods described herein may have at least 40%, 60%, 80%, 90%, 94%, 96%, 98%, 99.0%, 99.8% or 100% chiral purity.

In one embodiment, the prostacyclin derivative is treprostinil represented by structural formula (IX-1) (i.e., m=1 for structural formula (IX).

In one embodiment, for structural formulas (I)-(VI) and (A), R may be selected from the group consisting of methyl, benzyl, —CH$_2$COOMe, —CH$_2$COOCH$_2$Ph, THP and TBDMS. More specifically, R is methyl.

In another embodiment, for structural formulas (I)-(V), (A) and (a), P$_1$ is THP.

In yet another embodiment, for structural formulas (II) and (III), P$_2$ is TBDMS.

In another embodiment, for reactions depicted in Scheme 2, R is methyl, P$_1$ is THP, P$_2$ is TBDMS and m is 1.

In one embodiment, for methods of preparing a prostacyclin derivative described herein, specific conditions and reagents for reaction 1 are as described above.

For reaction 2 depicted in Scheme 2 above, compound (A) is reacted with an alcohol protecting reagent to form the compound of structural formula (II). An "alcohol protecting reagent" is a reagent that converts a —OH group to —OP$_2$. In one embodiment, the alcohol protecting reagent is TBDMSCl.

In one embodiment, reaction 2 is carried out in the presence of a base. Suitable base can be used includes, but is not limited to, an alkali carbonate, an alkali hydroxide, an amine and an ammonium hydroxide. More specifically, the base is an amine. Even more specifically, the base is a mixture of imidazole and dimethylaminopyridine (DMAP).

Reaction 2 can be carried out in a suitable solvent or a solvent mixture. In one embodiment, reaction 2 is carried out in an organic solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile. In one embodiment, the solvent is methylene chloride (CH$_2$Cl$_2$).

For reaction 3 depicted in Scheme 2, the compound of structural formula (II) is converted to the compound of structural formula (III) through a cobalt-mediated cyclization reaction. More specifically, the cyclization reaction is carried out in the presence of Co$_2$(CO)$_8$.

In one embodiment, reaction 3 is carried out in an organic solvent or a mixture of organic solvents. Suitable organic solvents include, but are not limited to, ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile. More specifically, reaction 3 is carried out initially in CH$_2$Cl$_2$ followed by removal of the solvent by distillation. The reaction is subsequently carried out in acetonitrile.

For reaction 4 depicted in Scheme 2, the compound of structural formula (III) is hydrogenated with H$_2$ to form the compound of structural formula (IV). In one embodiment, the hydrogenation reaction is carried out in the presence of a hydrogenation catalyst. More specifically, the hydrogenation reaction is carried out in the presence of Pd/C. In another embodiment, the hydrogenation reaction is carried out in the presence of a base, such as a alkali carbonate (e.g., K$_2$CO$_3$).

Reaction 4 can be carried out in an organic solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile. More specifically, the reaction is carried out in EtOH.

For reaction 5, the compound of structural formula (IV) is reacted with a reducing agent to form the compound of structural formula (V). A "reducing agent" is a reagent that can convert a carbonyl functional group to an alcohol functional group. Suitable reducing agents can be used include, but are not limited to, NaBH$_4$ and LiAlH$_4$. More specifically, the reducing agent is NaBH$_4$. In one embodiment, reaction 5 is carried out in the presence of a base, such as an alkali hydroxide (e.g. NaOH). Reaction 5 can be carried out in an organic solvent, such as those described above. More specifically, the reaction is carried out in EtOH.

For reaction 6, the compound of structural formula (V) is reacted with a strong acid, such as p-toluenesulfonic acid (pTsOH), TFA, TfOH, or hydrochloric acid, to form the compound of structural formula (VI). More specifically, the acid is pTsOH. Reaction 6 can be carried out in an organic solvent, such as those described above. More specifically, the solvent is MeOH.

For reaction 7, the compound of structural formula (VI) is reacted with Ph$_2$PH in the presence of a base. In one embodiment, the base is alkyllithium. More specifically, the base is nBuLi. Reaction 7 can be carried out in an organic solvent. Exemplary organic solvents are described above. In one embodiment, reaction 7 is carried out in tetrahydrofuran (THF).

For reaction 8, the compound of structural formula (VII) is reacted with X$_1$(CH$_2$)$_m$CN to form the compound of structural formula (VIII), wherein X$_1$ is a leaving group and m is 1, 2 or 3. A "leaving group" is a moiety that can easily be displaced by a nucleophile. For example, a leaving group is a halide (e.g., —Cl, —Br, —I), a sulfonate group (e.g., MeSO$_2$O—, CF$_3$SO$_2$O—, CH$_3$C$_6$H$_4$SO$_2$O—, or C$_6$H$_5$SO$_2$O—). More specifically, X$_1$ is —Cl and m is 1.

In one embodiment, reaction 8 is carried out in the presence of a base, such as an alkali carbonate (e.g., K$_2$CO$_3$).

Reaction 8 can be carried out in an organic solvent, such as those described above. More specifically, the solvent is acetone.

For reaction 9, the compound of structural formula (VIII) is reacted with a base, such as an alkali hydroxide (e.g., NaOH). The reaction can be carried out in an organic solvent, such as those described above. In one embodiment, the reaction is carried out EtOH.

Also included in the present invention is the prostacyclin derivatives represented by structural formula (IX) (e.g., treprostinil) prepared by methods described herein.

In some embodiments, a prostacyclin derivative represented by structural formula (IX), such as treprostinil, or a pharmaceutically acceptable salt thereof may be prepared using one or more reactions from Scheme 3:

In Scheme 3, $R_1$ may be an alkyl group or a substituted or unsubstituted benzyl group, and $P_1$ are as described above for structural formula (A); $P_2$ is an alcohol protecting group; and m is 1, 2, or 3.

Compound (7) in Scheme 3 corresponds to the prostacyclin derivative represented by structural formula (IX) earlier in the disclosure, compound (2) in Scheme 3 corresponds to the compound of structural formula (A) earlier in the disclosure, while Step 2 in corresponds to reaction 1 earlier in the disclosure.

In some embodiments, a method of preparing a prostacyclin derivative represented by structural formula (IX) or a pharmaceutically acceptable salt thereof may comprising Step 2 of Scheme 3. The method may also optionally include one or more steps selected from the group consisting of Step

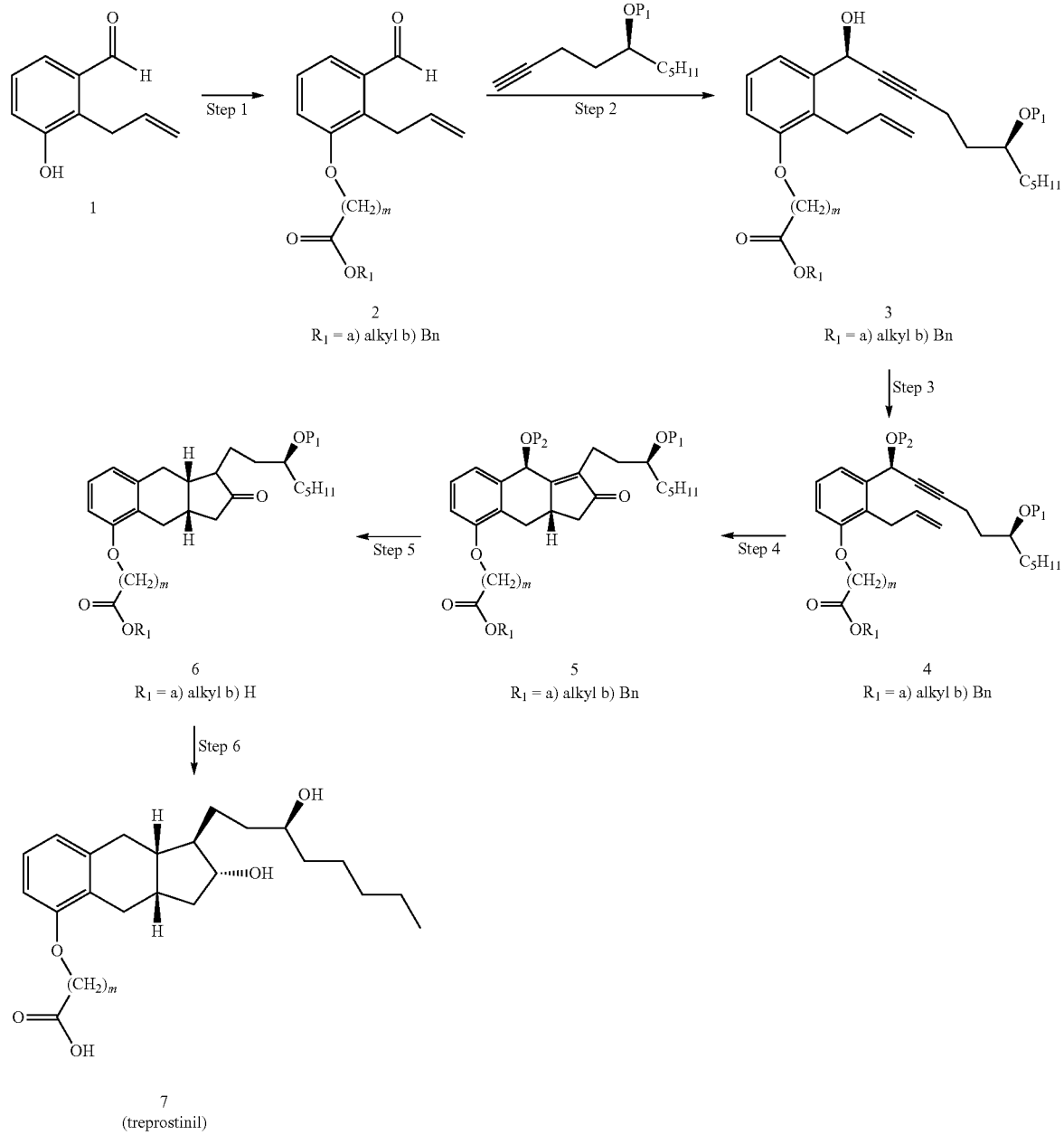

1, Step 3, Step 4, Step 5 and Step 6 shown in Scheme 3 in conjunction with Step 2 to make the prostaglandin derivative (IX). For example, the method comprises Step 2 and Step 3. Alternatively, the method may comprise Step 2, Step 3 and Step 4. In another alternative, the method may comprise the steps of Step 2, Step 5 and Step 6. In another alternative, the method may comprise Step 1 and Step 2. In yet another alternative, the method for preparing treprostinil may comprise Step 1, Step 2, Step 3, Step 4, Step 5 and Step 6.

The reactions of scheme 3 may be particularly useful for R is —$(CH_2)_m CO_2 R_1$, wherein m=1, 2 or 3 and $R_1$ is an alkyl group, such as a straight or branched C1-C5 alkyl group, or a substituted or unsubstituted benzyl group. Compared to prior art methods, such as those disclosed in U.S. Pat. Nos. 6,700, 025, 6,809,223, 6,528,668 and 6,441,245, the method of Scheme 3 may include fewer steps for preparing a prostacyclin derivative represented by structural formula (IX).

Step 1 of Scheme 3 may be performed by reacting compound 1 with $R_2 COOR_1$, wherein $R_2$ may be a leaving group such as halogen, e.g. Cl, I, or Br, tosylate, mesylate or triflate, and $R_1$ is an alkyl group or a substituted or unsubstituted benzyl group. In some embodiments, the reaction may be carried out in the presence of a base, which may be an alkali carbonate, such as $K_2 CO_3$. In some embodiments, the base may be potassium tertiary butoxide (t-BuOK), sodium hydride (NaH), sodium hydroxide (NaOH), lithium hydroxide (LiOH), potassium hydroxide (KOH) etc. The reaction may be carried out in a number of solvents including butanone, propanone, N,N-dimethyl formamide (DMF), dimethoxyethane (DME), dimethylsulfoxide (DMSO), tetrahydrofuran (THF), toluene and acetone.

Step 2 of Scheme 3 may be performed as described above for reaction 1 of scheme 2.

Step 3 of Scheme 3 may be performed by compound (A) with an alcohol protecting reagent to form the compound of structural formula (4). An "alcohol protecting reagent" is a reagent that converts a —OH group to —$OP_2$. In some embodiments, $P_2$ may be tert-butyldimethylsilyl (TBDMS), tertiarybutyldiphenylsilyl (TBDPS), triethylsilyl (TES) or triphenylmethyl (trityl group). The respective alcohol protective reagents may be TBDMSCl or TBDMSOTf for TBDMS, TESCl for TES, TBDPSCl for TBDPS and tritylchloride for trityl. In some embodiments, TBDMS may be preferred as $P_2$ and TBDMSCl may be preferred as the alcohol protecting reagent. Chemical formula of exemplary protective reagents is presented below.

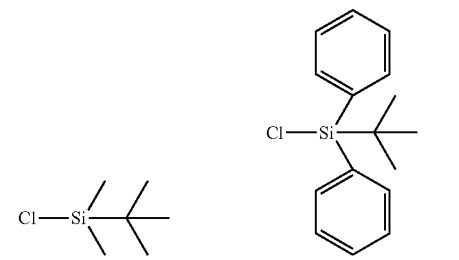

tert-butyldimethylsilyl chloride  tert-butyldiphenylsilyl chloride
TBDMSCl                           TBDPSCl

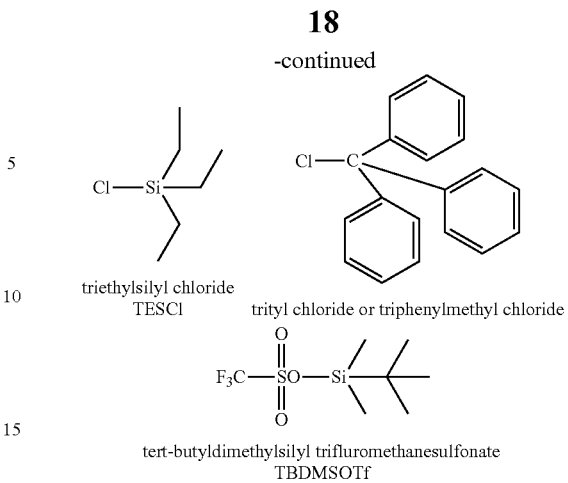

triethylsilyl chloride            trityl chloride or triphenylmethyl chloride
TESCl tert-butyldimethylsilyl trifluromethanesulfonate
TBDMSOTf In one embodiment, Step 3 of Scheme 3 may be carried out in the presence of a base. Suitable base that may be used includes, but is not limited to, an alkali carbonate, an alkali hydroxide, an amine and an ammonium hydroxide. In one specific embodiment, the base may an amine, such as of imidazole, 4-dimethylaminopyridine (DMAP) or a mixture thereof.

Step 3 of Scheme 3 may be carried out in a suitable solvent or a solvent mixture. In one embodiment, Step 3 of Scheme 3 may be carried out in an organic solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), dimethylformamide, dimethyl sulfoxide and acetonitrile. In one embodiment, the solvent may be methylene chloride ($CH_2 Cl_2$).

Step 4 of Scheme 3 may be performed by converting the compound of structural formula (4) to the compound of structural formula (5). In some embodiments, such conversion may be performed by a cobalt-mediated cyclization reaction. Such cyclization reaction may be carried out, for example, in the presence of $Co_2(CO)_8$.

In one embodiment, Step 4 of Scheme 3 may be carried out in an organic solvent or a mixture of organic solvents. Suitable organic solvents include, but are not limited to, ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile. In some embodiments Step 4 of Scheme 3 may be carried out in 1,2-dimethoxyethane. followed by removal of the solvent by distillation.

In some embodiments, Step 4 may be carried out using from about 2 to 15 mol % or from 3 to 12 mol % or from 5 to 10 mol % or any subrange within the above stated ranges of $Co_2(CO)_8$. In some embodiments, Step 4 may be carried out under atmosphere of carbon monoxide using from about 2 to 15 mol % or from 3 to 12 mol % or from 5 to 10 mol % or any subrange within the above stated ranges of $Co_2(CO)_8$. Such conditions may save cost and/or avoid laborious column chromatography and hence save time compared to stoichiometric Pauson-Khand cyclization such as the one used, for example, in U.S. Pat. No. 6,765,117.

In some embodiments, the reaction of Step 4 may be carried out under atmospheric pressure. Yet in some embodiments, the reaction of step of Step 4 may be carried at a pressure that is higher than the atmospheric pressure. The use of the elevated pressure may make the reaction of Step 4 go faster compared the reaction under the atmospheric pressure. In some embodiments, the reaction of Step 4 may be carried out at a pressure ranging from 10 psi to 250 psi or from 20 psi to 250 psi or from 20 psi to 200 psi or any subrange within these ranges.

Step 5 of Scheme 3 may be performed by hydrogenating the compound of structural formula (5) to form a hydrogenated compound of formula (6) or (6'). The hydrogenation reaction may involve reacting the compound of structural formula (5) with $H_2$. In some embodiments, the hydrogenation reaction may be carried out in the presence of a hydrogenation catalyst. Such hydrogenation catalyst may comprise a metal hydrogenation catalyst, such as Pd. In some embodiments, the hydrogenation catalyst may be Pd/C. In some embodiments, the hydrogenation reaction may be carried out in the presence of a base, which may be a alkali carbonate, such as $K_2CO_3$.

Step 5 of Scheme 3 may be carried out in an organic solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, 2-propanol), dimethylformamide, dimethyl sulfoxide and acetonitrile.

When $R_1$ is an alkyl group Step 5 may result in the hydrogenated compound of structural formula (6):

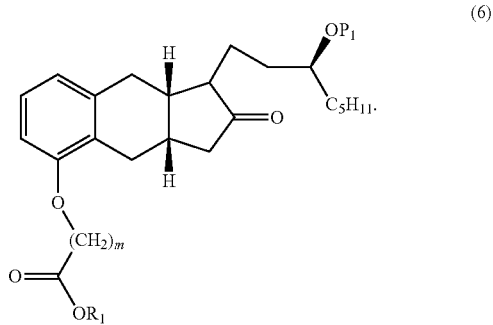

(6)

When $R_1$ is a substituted of unsubstituted benzyl group Step 5 may result in the hydrogenated compound of structural formula (6'):

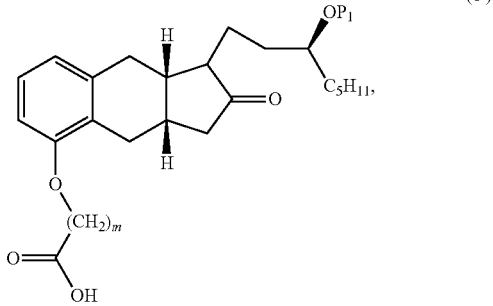

(6')

which has its benzyl group cleaved as the result of hydrogenation.

Step 6 of Scheme 3 may be performed by converting the hydrogenated compound represented by structural formula (6) or (6') to a compound represented by structural formula (7) or (IX). In some embodiments, the conversion of Step 6 may be performed in the presence of a reducing agent, which may be used for the reduction of the ketone to alcohol on the cyclopentyl ring. The reducing agent may be, for example, $NaBH_4$, $NaCNBH_3$ or $LiBH_4$. In some embodiments, the reducing agent may be used together with a base, which may be used for hydrolysis of the ester group to acid. The base may be, for example, NaOH, KOH, LiOH or $Ba(OH)_2$. In some embodiments, step 6 may be carried in the presence of an acid, which may be used to obtain a free acid from the ester group after its hydrolysis and/or to remove the protection group $P_1$ from the side chain. In some embodiments, the acid may be, for example, HCl, acetic acid, formic acid, trifluoroacetic acid, para-toluene sulfonic acid, dilute $H_2SO_4$, dilute $HNO_3$ or a polymer bound acidic resin, such as Amberlyst-15 or Dowex 50WX-X8. Solvents, which may be used for Step 6's conversion, may include water and/or organic solvents, such as alcohols, for example ethanol. In some embodiments, Step 6 may be performed in the presence of two or more of the reducing agent, the base and the acid. In some embodiments, Step 6 may be carried out in the presence of all three of the reducing agent, the base and the acid.

Step 6 may allow performing one or more of the following in a single pot: reduction of the ketone of compound (6) to alcohol of compound (7), hydrolysis of the ester group of compound (6) to a free acid of compound (7) and removal of the $P_1$ protective group of compound (6).

For example, conversion of compound of structural formula (6), when $R_1$ is an alkyl group, the conversion reaction may accomplish cleaving of the protective group $P_1$ and ester hydrolysis of R to a free acid in a single pot. This conversion may also include reduction of the ketone of compound (6) to alcohol of compound (7).

The present invention also relates to intermediates for synthesis a prostacyclin derivative represented by structural formula (IX), such as compounds of formulas (2), (3), (4), (5) and (6, 6') in Scheme 3.

The invention is further illustrated by, though in no way limited to, the following examples.

EXAMPLE 1

Preparation of Chiral Benzyl Alcohol (A-1)

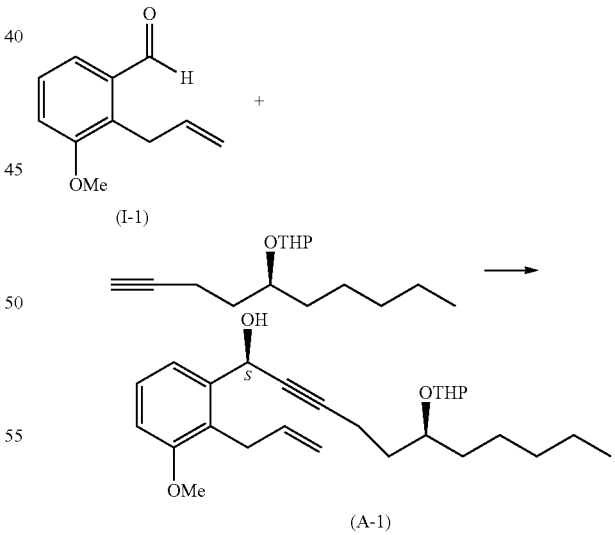

A 50-mL, two-necked, round-bottom flask equipped with a mechanical stirrer was charged with zinc triflate (2.16 g, 0.0059 mol) and (+)-N-methylephiderine (0.814 g, 0.0045 mol) in toluene (10 mL). To this mixture triethyl amine was added (0.459 g, 0.0045 mol) and this gelatinous mixture was stirred at ambient temperature for 30-60 minutes. To this mixture was then treated with a solution of alkyne (1.08 g, 0.0045 mol) in toluene (1 mL), stirred at ambient temperature for 15 minutes followed by solution of aldehyde (0.250 g, 0.0014 mol). Progress of the reaction was monitored by TLC (completion of the reaction was monitored by thin layer chromatography (TLC) using a thin layer silica gel plate; eluent: 20% ethyl acetate in hexanes). After stirring the mixture for 3 h TLC indicated completion of reaction. At this stage reaction mixture was quenched by slow addition of saturated ammonium chloride (10 mL). This was stirred for 5-10 minutes and organic layer containing desired compound was separated. Aqueous layer was washed with ethyl acetate (10 mL). The combined organic layers were washed with brine (15 mL), dried over anhydrous sodium sulfate, filtered and concentrated in vacuo to obtain a crude product (2.0 g). The crude product was purified by column chromatography using 250-400 mesh silica gel. A solvent gradient of ethyl acetate in hexanes (5-20%) was used to elute the product from the column. All fractions containing the desired product were combined and concentrated in vacuo to give pure chiral benzyl alcohol A-1 (0.360 g, ~87%) compound was characterized by $^1$H, $^{13}$C NMR, IR, LCMS and chiral HPLC data. $^1$H NMR (CDCl$_3$, 300 MHz): δ 0.87 (t, 3H), 1.18-1.86 (m, 17H), 2.28 (dt, 1H), 2.34-2.45 (m, 2H), 3.40-3.53 (m, 1H), 3.54-3.62 (m, 1H), 3.63-3.75 (m, 1H), 3.81 (s, 3H, OCH3), 3.83-3.92 (m, 1H), 4.62-4.66 (m, 1H), 4.89-5.05 (m, 2H), 5.59-5.61 (merged two s, 1H), 5.91-6.04 (m, 1H), 6.85-6.82 (d, 1H), 7.20-7.26 (m, 1H), and 7.31-7.36 (m, 1H); $^{13}$C NMR (CDCl$_3$, 75 MHz): δ 14.13, 14.18, 14.98, 15.56, 19.96, 21.14, 22.71, 24.77, 25.34, 25.57, 29.51, 31.17, 31.23, 32.07, 32.19, 32.69, 33.51, 33.94, 35.13, 55.86, 60.49, 62.12, 62.18, 62.82, 75.36, 75.89, 80.20, 80.53, 86.97, 87.42, 97.31, 98.06, 110.63, 114.80, 119.18, 119.27, 125.86, 127.44, 127.50, 137.15, 140.78, 157.68; IR: 3411, 2230, 1638, 1259, 1133, 1023, 755 cm$^{-1}$; MS (m/z): [M+Na]$^+$ 437.35.

EXAMPLE 2

Preparation of Treprostinil (IX-1)

Treprostinil can be prepared according to Scheme 4. Exemplary reaction conditions for making the chiral benzyl alcohol (compound A-1) are described in Example 1. Exemplary conditions for other reactions depicted in Scheme 3 are as described in U.S. Pat. Nos. 6,700,025, 6,809,223, 6,528,668 and 6,441,245. The entire teaching of all these documents are incorporated herein by reference.

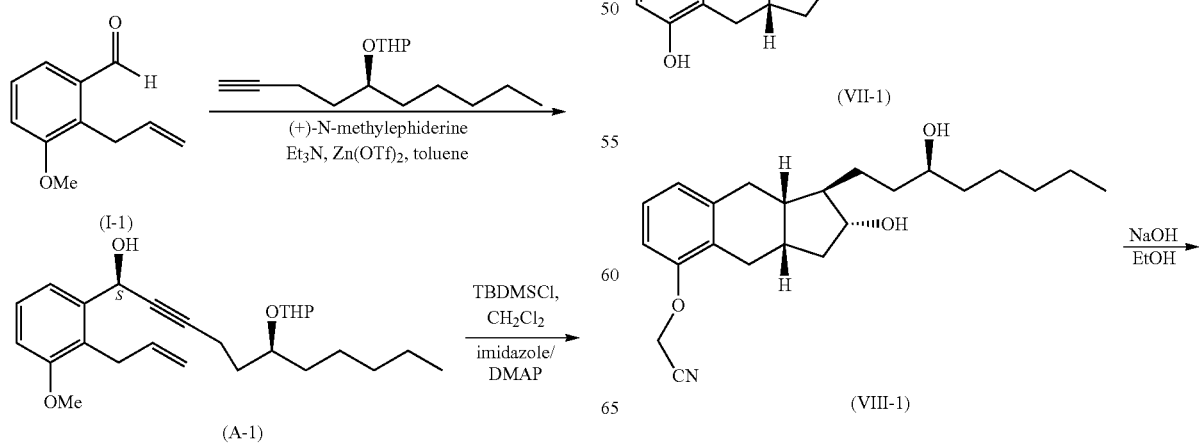

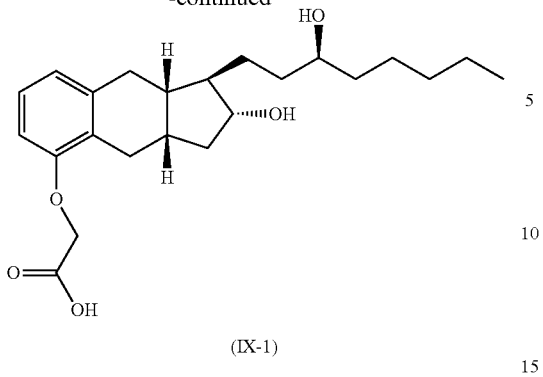
(IX-1)
EXAMPLE 3
Preparation of Treprostinil
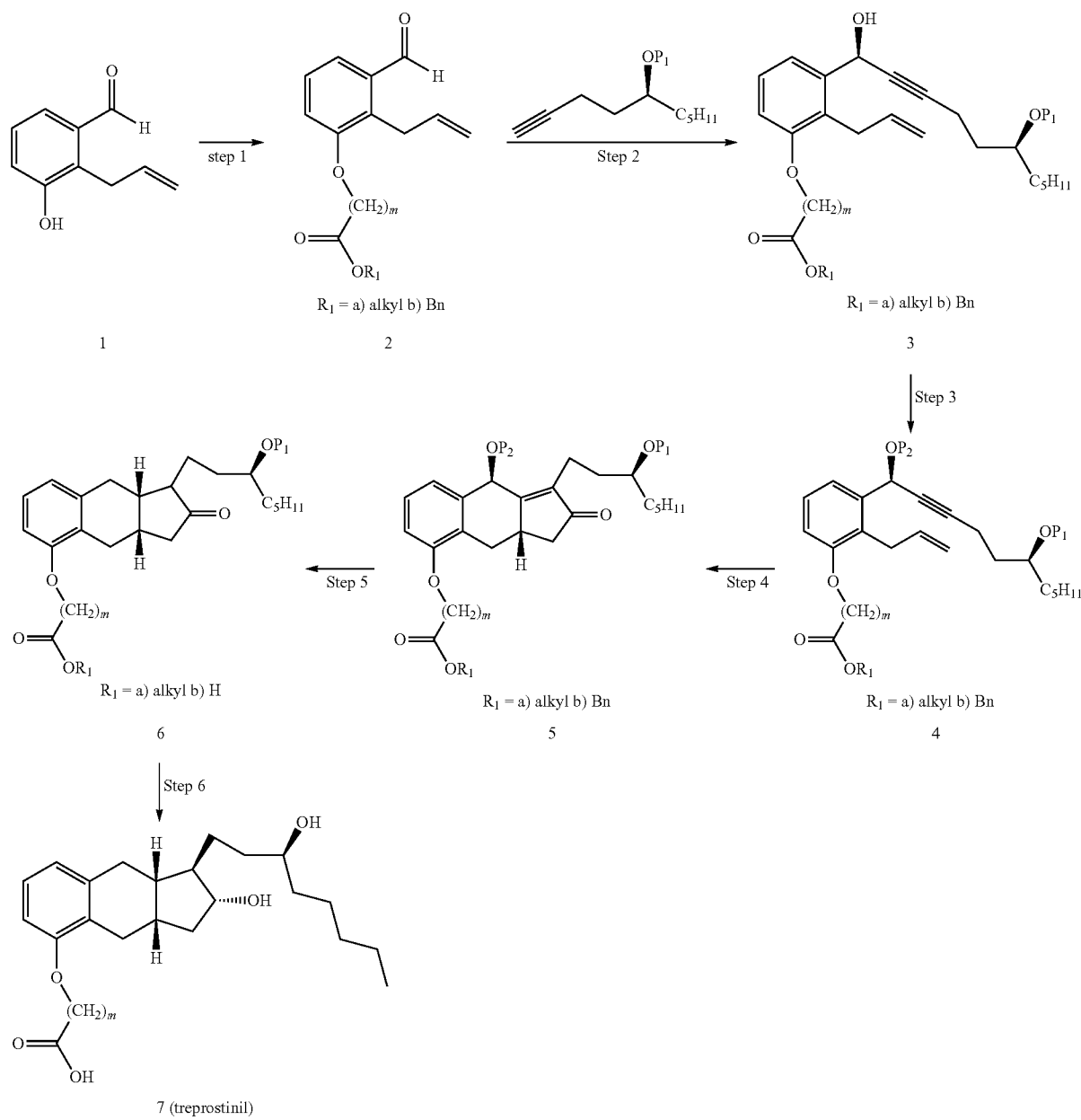

The inventors have developed a stereoselective route for the synthesis of treprostinil (7) starting from aldehyde (1) and side chain (SCiv). This route may involve direct stereoselective addition of an alkyne to starting 2-Allyl-3-[(carbomethoxy)methoxy]benzaldehyde (2) and illustrates the synthetic utility of catalytic a Pauson-Khand Cyclization (PKC) for the synthesis of a drug substance, treprostinil (7, UT-15). O-alkylation of the readily available 3-hydroxy-2-allylbenzaldehyde (Step 1→2) with methylbromoacetate provided the required starting material (2) to accomplish this synthesis. The steps in the synthesis may involve a stereoselective addition of an alkyne, and an efficient stereoselection effected in the PKC of a benzoenyne under the agency of a protective group $P_1$, such as benzylic OTBDMS group. This protective group can serve as a temporary stereodirecting group and may be conveniently removed via hydrogenolysis concomitantly in the catalytic hydrogenation of the enone PKC product. At the final step, reduction, $P_1$ cleavage and ester hydrolysis may be accomplished in one pot to obtain desired prostaglandin analog product, such as treprostinil (7).

The advantage of the present chemistry may include, but not limited to: 1) direct stereoselective addition of alkyne to aldehyde; 2) this route may also eliminate the need of four steps in the prior art synthesis of prostacyclin derivatives disclosed, for example, in Moriarty et al (U.S. Pat. No. 6,765,117). In particular, the present route may eliminate one or more of the following steps of the prior art synthesis (U.S. Pat. No. 6,765,117):

1) Grignard addition step (compound 5-compound 6 in U.S. Pat. No. 6,765,117);

2) PCC oxidation step (compound 6-compound 7 in U.S. Pat. No. 6,765,117);

3) Chiral reduction step, aka as Corey reduction (compound 7-compound 8 in U.S. Pat. No. 6,765,117);

4) demethylation of phenyl methyl ester (compound 13-compound 14 in U.S. Pat. No. 6,765,117).

The present synthesis scheme may not only shorten the number of chemical steps to obtain treprostinil but also eliminate the tedious column chromatographic purifications required in the prior art methods, such as the one in U.S. Pat. No. 6,765,117 at intermediate steps. Such elimination of the prior art chromatographic purifications may significantly save manpower and large volumes of solvents. For example, the prior art route of U.S. Pat. No. 6,765,117 has 15 steps and requires chromatographic purifications on all them but one (compound II-compound 12). The present synthesis has only 6 steps and may include chromatographic purification in at most three steps (steps 2, step 3 and step 4).

The present synthesis scheme may enable performing the reactions at room temperature without the need for cryogenic reactors, which are required in the prior art methods, such as the one in U.S. Pat. No. 6,765,117. For example, the prior art route of U.S. Pat. No. 6,765,117 requires cryogenic reactors in chiral reduction step (compound 7-compound 8) and in demethylation of phenyl methyl ester (compound 13-compound 14).

The present synthesis does not involve use of expensive reagents which are required in the prior art methods, such as the one in U.S. Pat. No. 6,765,117. For example, the prior art route of U.S. Pat. No. 6,765,117 in the chiral reduction step (compound 7-compound 8) used starting compound (B) for Corey reagent (B+C), which is an expensive reagent. Corey reagent (B+C) itself is also an expensive reagent.

This report provides the experimental details on the synthesis of treprostinil (7) below.

Step 1:
2-Allyl-3-[(carbomethoxy)methoxy]benzaldehyde (2)

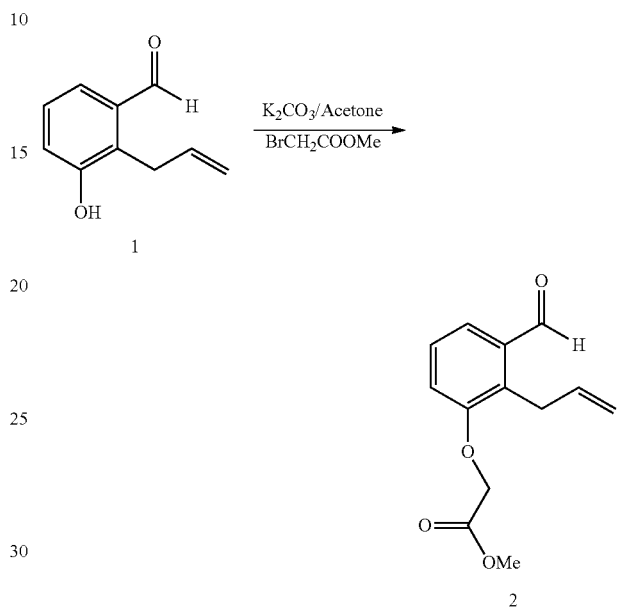

TABLE 1

| Name | MW | Amount | mol |
|---|---|---|---|
| Aldehyde (1) | 162.18 | 2.5 g | 0.015 |
| methylbromoacetate | 152.97 | 2.5 g | 0.016 |
| $K_2CO_3$ | 138.21 | 6.3 g | 0.045 |
| Acetone | NA | 50 ml | NA |

Procedure: A 100-mL round-bottom flask equipped with a magnetic stirrer and stir bar was charged with a solution of 3-hydroxy-2-allylbenzaldehyde (1) (2.5 g in 50 mL acetone), methylbromoacetate (2.5 g, 1.10 eq.) and powdered potassium carbonate (6.3 g, 3.0 eq.). The mixture was stirred at 40° C. for four hours and progress of reaction was monitored by TLC (Note 1). After completion of the reaction, the suspension was filtered and the filtrate was evaporated in vacuo to afford a crude semi-solid mass. This was slurried in 30 mL of hexanes and stirred for 15 minutes. A solid crashed out of the hexanes and was collected by filtration to obtain compound (2) as an off-white solid; yield 3.48 g (99%), mp 46-47° C. The structure was consistent with spectral data. IR (neat) $cm^{-1}$: 3084, 2761, 1735, 1692; $^1$H NMR ($CDCl_3$, 300 MHz) δ 3.78 (s, 3H), 3.91 (d, 2H, J=6 Hz), 4.71 (s, 2H), 4.98 (m, 2H), 6.03 (m, 1H), 6.96 (d, 1H, J=8 Hz), 7.33 (dd, 1H, J=8 Hz), 7.52 (d, 1H, J=8 Hz); $^{13}$C NMR ($CDCl_3$, 75 MHz) δ 28.32, 52.37, 66.01, 115.75, 117.05, 123.73, 127.55, 131.73, 135.40, 136.58, 156.23, 169.09, 192.08; MS: (M+1) 235.41.

Note 1: Completion of the reaction was monitored by TLC using a thin layer silica gel plate; eluent: 20% ethyl acetate in hexanes.

Step 2: Preparation of Chiral Benzyl Alkynol (3)

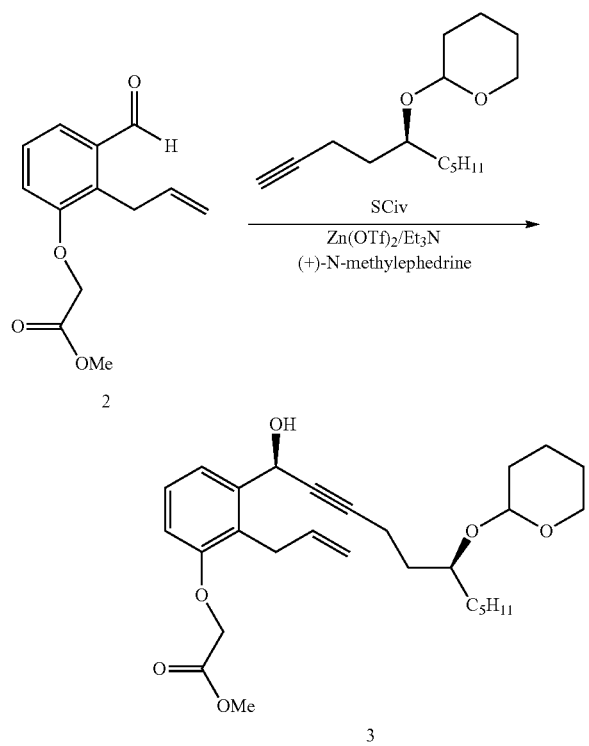

TABLE 2

| Name | MW | Amount | mol |
|---|---|---|---|
| Aldehyde (2) | 234.25 | 0.50 g | 0.0026 |
| Alkyne side chain (Sciv) | 238.37 | 1.57 g | 0.0065 |
| Zinc triflate | 363.51 | 3.17 g | 0.0087 |
| (+)-N-Methylephedrine | 179.26 | 1.22 g | 0.0068 |
| Triethylamine | 101.19 | 0.68 g | 0.0068 |
| Toluene | NA | 10 ml | NA |

Procedure: A 50-mL, two-necked, round-bottomed flask equipped with a magnetic stirrer and stir bar was charged with zinc triflate (3.17 g, 0.0087 mol) and (+)-N-methylephedrine (1.22 g, 0.0068 mol) in toluene (5 mL). To this mixture triethylamine was added (0.68 g, 0.0068 mol) and this gelatinous mixture was stirred at ambient temperature for 1-2 h. To this mixture was then added a solution of alkyne (1.57 g, 0.0065 mol) in toluene (4 mL), stirred at ambient temperature for 15-30 minutes followed by addition of a solution of aldehyde (2) (0.50 g, 0.0026 mol in 1-2 mL toluene). Progress of the reaction was monitored by TLC (Note 1). After stirring the mixture at room temperature for 16 h, TLC indicated completion of reaction. The reaction mixture was quenched by slow addition of water (10 mL). This was stirred for 5-10 minutes and organic layer containing desired compound was separated. The aqueous layer was extracted with ethyl acetate (10 mL). The combined organic layers were washed with brine (10 mL), dried over anhydrous sodium sulfate, filtered and the filtrate concentrated in vacuo to obtain a crude product. The crude product wa~ purified by column chromatography using 250-400 mesh silica gel. A solvent gradient of ethyl acetate in hexanes (5-20%) was used to elute the product from the column. All fractions containing the desired pure product were combined and concentrated in vacuo to give pure chiral benzyl alkynol (3,700 mg, ~70%). The structure was consistent with spectral data.

$^1$H NMR (CDCl$_3$, 300 MHz) δ 0.84 (t, 3H, J=6 Hz), 1.25-1.82 (m, 17H), 2.28 (t, 1H, J=6 Hz), 2.34-2-42 (m, 2H), 3.42-3.52 (m, 1H), 3.61-3.74 (m, 3H), 3.78 (s, 3H), 3.81-3.95 (m, 1H), 4.61 (s, 2H), 4.68 (m, 1H), 4.94-5.01 (m, 2H), 5.62 (br s, 1H), 5.97-6.07 (m, 1H), 6.76 (d, 1H, J=8 Hz), 7.16-7.27 (m, 1H), 7.38-7.43 (m, 1H); $^{13}$C NMR (CDCl$_3$, 75 MHz) δ4.75, −4.38, −3.49, 14.12, 14.16, 14.84, 15.52, 18.06, 18.38, 20.04, 20.24, 22.70, 24.76, 25.25, 25.56, 25.72, 25.94, 29.67, 31.22, 31.28, 32.05, 32.11, 32.65, 33.41, 34.01, 35.08, 52.22, 62.36, 62.84, 63.09, 66.04, 75.41, 76.44, 76.68, 80.83, 81.22, 85.57, 86.01, 97.31, 98.85, 110.89, 114.80, 119.77, 119.82, 125.56, 127.11, 127.16, 136.46, 136.52, 142.66, 142.73, 155.83, 169.68; MS: (M+Na) 495.6.

Note 1: Completion of the reaction was monitored by thin layer chromatography (TLC) using a thin layer silica gel plate; eluent: 20% ethyl acetate in hexanes.

Step 3: Preparation of Chiral Benzylalkynyl tert.-butyldimethylsilyl ether (4)

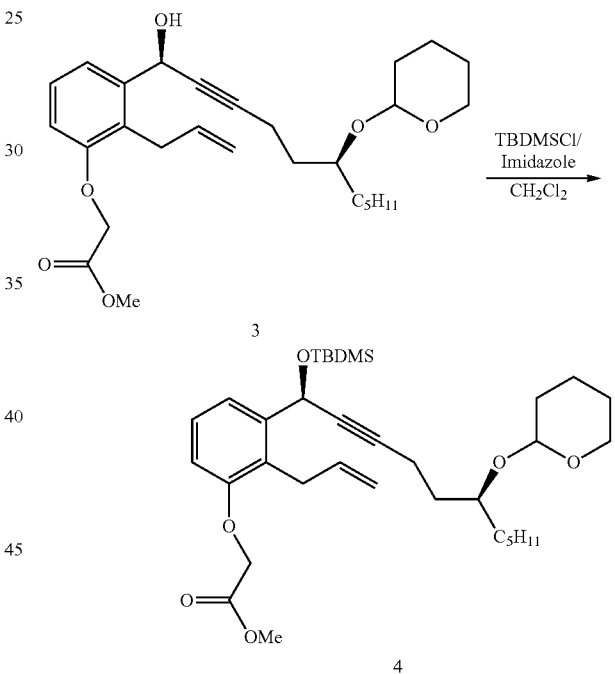

TABLE 3

| Name | MW | Amount | Mol |
|---|---|---|---|
| Chiral benzylalkynol | 472.62 | 0.680 g | 0.0014 |
| t-butyldimethylsilyl chloride | 150.73 | 0.282 g | 0.0018 |
| Imidazole | 68.0 | 0.127 g | 0.0018 |
| 4-(Dimethylamino)pyridine | 122.17 | 0.167 g | 10 mol % |
| Dichloromethane | NA | 30.0 mL | NA |

Procedure: A 50-mL, two-necked, round-bottomed flask equipped with a magnetic stirrer and stir bar was charged with a solution of chiral benzylalkynol (3) (0.680 g, 0.0014 mol) in dichloromethane (30 mL) under argon. To this solution, imidazole (0.127 g, 0.0018 mol) and 4-(dimethylamino)pyridine (0.176 g, 10 mol %) were added while stirring at room temperature. The stirring was continued until a clear solution was obtained. To this solution t-butyldimethylsilyl chloride (0.282 g, 0.0018 mol) was added slowly while stirring. The reaction mixture was stirred at room temperature for approximately 3-4 h (Note 1). The reaction was quenched by addition of a saturated ammonium chloride solution (10 mL). The organic layer was separated and washed with brine (10 mL), dried over sodium sulfate and concentrated in vacuo. The crude product was purified by column chromatography using 250-400 mesh silica gel and eluted with a gradient solvent of ethyl acetate in hexanes (2-12%). The fractions containing the desired compound were evaporated in vacuo to yield benzyl alkynyl t-butyldimethylsilyl ether (4) as a colorless, viscous liquid (0.800 g, 94%). The structure was consistent with spectral data. $^1$H NMR (CDCl$_3$, 300 MHz) δ 0.07-0.13 (four merged s, 6H), 0.83 (merged t, 3H), 0.89-0.91 (two merged s, 9H), 1.24-1.84 (m, 10H), 2.18-2.34 (m, 2H), 3.39-3.69 (m, 3H), 3.78 (s, 3H), 3.81-3.91 (m, 1H), 4.55-4.56 (m, 1H), 4.62 (s, 2H), 4.96-4.98 (m, 2H), 5.57 (br s, 1H), 5.92-6.01 (m, 1H), 6.66 (d, 1H, J=8 Hz), 7.17 (two dd, 1H, J=8 Hz), 7.30 (d, 1H, J=8 Hz).

Note 1: Completion of the reaction was monitored by TLC using a thin layer silica gel plate; eluent: 20% ethyl acetate in hexanes.

Step 4: Preparation of Tricyclicenone (5)

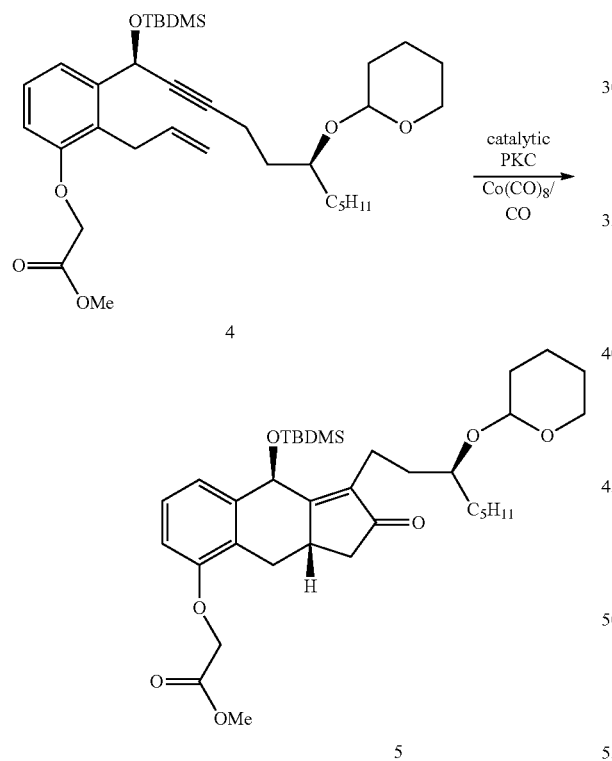

TABLE 4

| Name | MW | Amount | Mole |
| --- | --- | --- | --- |
| Benzyl alkynyl t-butyldimethylsilyl ether (4) | 584.65 | 0.100 g | 0.00017 |
| Octacarbonyldicobalt | 341.95 | 0.0030 | 5 mol % |
| 1,2-Dimethoxyethane | NA | 10 ml | NA |

Procedure: A 50-mL round-bottomed flask equipped with a magnetic stirrer and stir bar was charged with a solution of benzylalkynyl tert.-butyldimethylsilyl ether (4) (0.10 g) in 1,2-DME (10 mL), and was degassed by bubbling argon through the solution for 2-3 minutes. To this solution was added CO$_2$(CO)$_8$ (0.003 g) and the mixture was stirred at room temperature under an atmosphere of carbon monoxide (CO, using balloon). After 30 minutes the reaction mixture was heated to 60-65° C. using an oil bath for 6 h (Note 1). After cooling to room temperature, 1,2-DME (solvent) was evaporated in vacuo to yield a crude, gummy compound that was purified by flash chromatography on silica gel using 5-20% ethyl acetate in hexanes. Fractions containing the desired compound were collected and evaporated in vacuo to yield tricyclic enone (5) (102 mg, 83%). The structure was consistent with spectral data. IR (neat) cm, 1: 2928, 1728, 1702; $^1$H NMR (CDCl$_3$, 300 MHz) δ 0.02-0.13 (m, 6H), 0.80 (merged s, 9H), 0.81-0.88 (m, 1H). 1.18-2.61 (m, 16H), 2.71 (dd, 1H, J=6 Hz), 3.32-3.60 (m, 4H), 3.79 (merged s, 3H), 3.80-3.92 (m, 1H), 4.56 (merged d, 1H), 4.60 (merged s, 2H), 5.47 and 5.53 (two s, 1H), 6.63, 1H, J=8 Hz), 6.97 (dd, 1H, J=8 Hz), 7.19 (dd, 1H, J=8 Hz); $^{13}$C NMR (CDCl$_3$, 75 MHz) δ 4.20, 4.08, 14.17, 18.15, 20.13, 22.69, 24.84, 25.71, 31.27, 32.14, 33.29, 33.93, 42.19, 52.34, 62.86, 65.50, 76.68, 97.24, 110.19, 123.28, 125.74, 127.31, 137.52, 137.95, 155.18, 169.44, 209.60.

Note 1: Completion of reaction was monitored by TLC using a thin layer silica gel plate; eluant: 20% ethyl acetate in hexanes. After 3 h, TLC showed presence of starting material. At this stage extra 5 mol % cobalt catalyst was added at room temperature and reaction was again heated at 60-65° C. until completion (total reaction time 6 h)

Step 5: Preparation of Tricyclic Ketone (6)

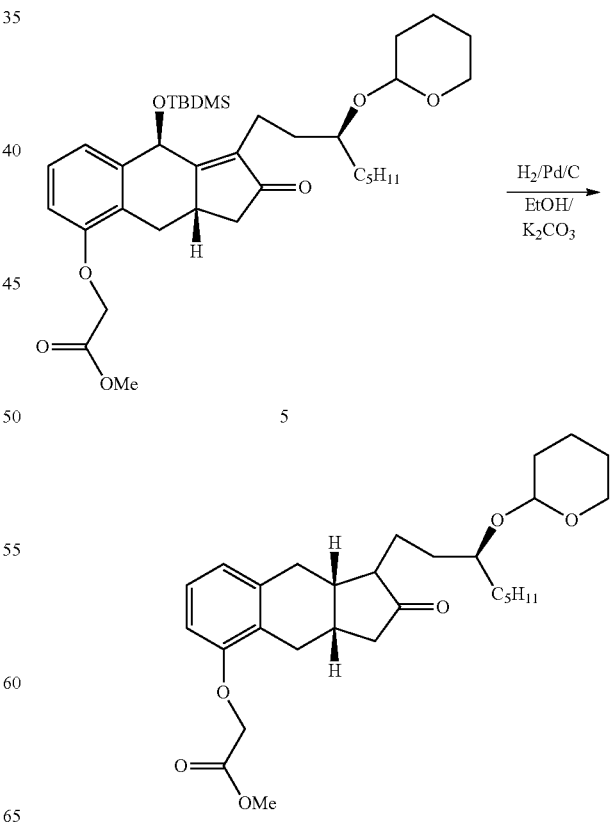

TABLE 5

| Name | MW | Amount | Mole |
|---|---|---|---|
| Tricyclic enone (5) | 614.90 | 0.10 g | NA |
| Palladium on charcoal (50% wet) | NA | 0.01 g | NA |
| Potassium carbonate | NA | 0.010 | NA |
| Methanol | NA | 10.0 ml | NA |
| Water | NA | 1.00 ml | NA |

Procedure: A 200-mL round-bottom flask equipped with a magnetic stirrer and stir bar was charged with a solution of tricyclic enone (5) (0.10 g) in methanol (10.0 mL) and aqueous $K_2CO_3$ (0.010 g in 1.0 mL water). To this solution, Pd/C (0.010 g, 50% wet) was added while stirring at room temperature. The reaction vessel was evacuated and pressurized with hydrogen gas using a balloon. The reaction mixture was hydrogenated at balloon pressure overnight (~16 h) at ambient temperature. After 16 h, the reaction was monitored by TLC, infra-red (IR) and proton NMR (Note 1). At this stage the reaction mixture was filtered through a pad of Celite (~4 g). The Celite pad was washed with methanol (~50 mL). The combined filtrates were evaporated in vacuo to give crude tricyclic ketone (6) and the crude product was purified by column chromatography using 250-400 mesh silica gel. A solvent gradient of ethyl acetate in hexanes (5-35%) was used to elute the product from column. The fractions containing desired product were evaporated in vacuo to yield tricyclic ketone (6) (0.035 g, 44%). IR (neat) $cm^{-1}$ 2929, 1736, 1679; $^1$H NMR ($CDCl_3$, 300 MHz) δ 0.87 (br t, 3H), 1.21-3.12 (m, 27H), 3.42-3.53 (m, 1H), 3.55-3.68 (m, 1H), 3.79 (s, 3H), 3.86-3.95 (m, 1H), 4.61-4.69 (m, 1H), 4.64 (merged s, 2H), 6.53-6.56 (m, 1H), 6.74-6.81 (m, 1H), 7.06-7.08 (m, 1H).

Note 1: Completion of the hydrogenation was checked by monitoring the change in the IR carbonyl stretch frequency [starting material (tricyclic enone) ~1728 $cm^{-1}$, product (tricyclic ketone) ~1736 $cm^{-1}$ and proton NMR. The reaction mixture was evacuated and then purged with argon. A small aliquot of reaction mixture was sampled, filtered through a short pad of Celite, and the filtrate was evaporated in vacuo to give a thick, oily compound. The IR of the oily compound was checked for above mentioned carbonyl stretch frequency. Completion of reaction was monitored by TLC using a thin layer silica gel plate; eluent: 40% ethyl acetate in hexanes.

Step 6: Preparation of Treprostinil (7)

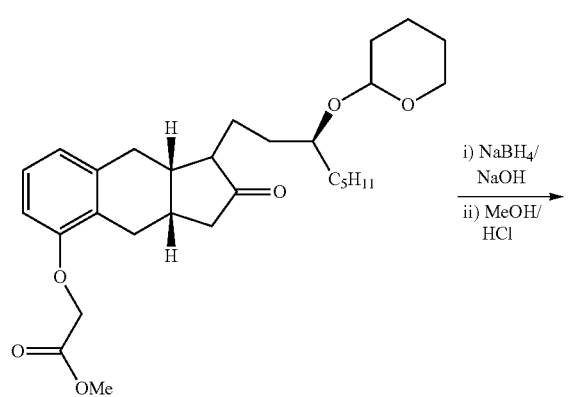

6

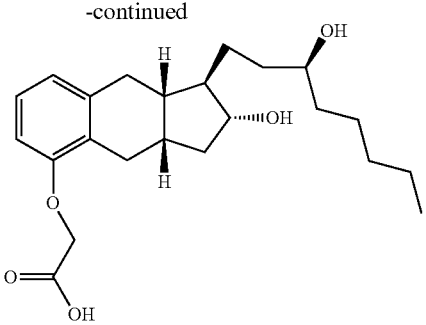

7 (treprostinil)

TABLE 6

| Name | MW | Amount | Mole |
|---|---|---|---|
| Tricyclic ketone (6) | 486.65 | 0.0035 g | 0.00006 |
| Sodium hydroxide | 40.0 | 0.030 g | 0.00073 |
| Sodium borohydride | 37.8 | 0.004 g | 0.00012 |
| Methanol | NA | 5.0 ml | NA |
| Water | NA | 1.0 ml | NA |
| HCl | NA | (10%) 4-5 ml | NA |

Procedure: A 200-mL round-bottom flask equipped with a magnetic stirrer and stir bar was charged with a solution of tricyclic ketone (6) (0.035 g) in methanol (5.0 mL). It was cooled to −5° C. and aqueous sodium hydroxide solution (0.030 g, 15 eq, dissolved in 1.0 mL water) was added while stirring. The reaction mixture was stirred for 30 minutes and then sodium borohydride (0.004 g in 1.0 mL water) was added and stirring was continued at −5° C. for 2 h. This was slowly allowed to warm to room temperature and stirred overnight (~16 h). The reaction mixture was quenched carefully by dropwise addition of 10% hydrochloric acid (~4-5 mL) until pH 2-3. Then the mixture was concentrated in vacuo and to this water (10 mL) and ethyl acetate (10 mL) were added and stirred for 5-10 minutes. The organic layer was separated and washed with brine (10 mL), dried over sodium sulfate and concentrated in vacuo to obtain UT-15 (7) as an off-white solid (0.021 g). The compound was characterized by spectral data and HPLC. The $^1$HNMR and HPLC of the samples were compared with reference UT-15 and were identical; $^1$H NMR ($CDCl_3$, 300 MHz) δ 0.90 (t, 3H, 6 Hz), 1.05-1.78 (m, 13H), 2.85-2.85-2.98 (m, 1H), 2.03 2.12 (m, 1H), 2.21-2.32 (m, 1H), 2.45-2.53 (m, 1H), 2.61-2.81 (m, 3H), 3.52 (br s, 1H), 3.58-3.69 (m, 1H), 4.62 (s, 2H), 6.69 (d, 1H, J=8 Hz), 6.78 (d, 1H, J=8 Hz), 7.04 (dd, 1H, J=8 Hz).

EXAMPLE 4

Preparation 2-Ally-3-(carbomethoxy)benzyloxybenzaldehyde

Reaction Scheme:

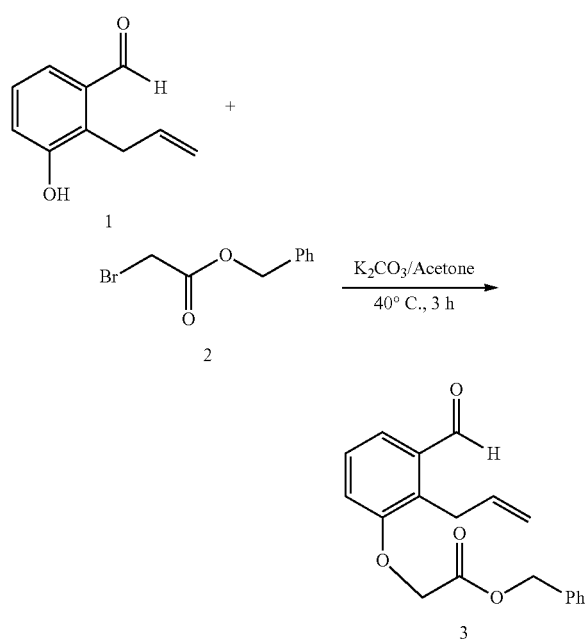

EXPERIMENTAL

Preparation of 2-Allyl-3-benzyloxybenzaldehyde (3)

TABLE 7

| Name | Mol Wt | Amount | mol |
| --- | --- | --- | --- |
| 2-Allyl-3-hydroxybenzaldehyde | 162.18 | 1.00 g | 0.006 |
| Benzyl bromoacetate | 229.08 | 1.53 g | 0.006 |
| Potassium carbonate | 138.21 | 3.30 g | 0.024 |
| Acetone | NA | 20 mL | NA |

Experimental Procedure

To a solution of 2-allyl-3-hydroxybenzaldehyde (1) (1.00 g, 0.006 mol) in acetone (20 mL) was added powdered potassium carbonate (3.30 g) and benzyl bromoacetate (2) (1.53 g, 0.006 mol). The reaction mixture was stirred at 40° C. (oil bath temperature) for 5 h. The reaction mixture was checked by tlc (Note 1). The reaction was complete. The mixture was filtered, and the filtrate was concentrated in vacuo to get crude viscous liquid. The crude product was purified by silica gel column chromatography using a mixture of ethyl acetate and hexanes (4-10%) to get colorless viscous liquid (1.73 g, 88.7%). $^1$H NMR (CDCl$_3$, 300 Hz) 3.89 (m, 2H), 4.74 (s, 2H), 4.95-5.00 (m, 2H), 5.22 (s, 2H), 5.97-6.06 (m, 1H), 6.97 (m, 1H), 7.29-7.34 9m, 6H), 7.54 (m, 1H).

Note 1: Completion of the reaction was monitored by thin layer chromatography (TLC) using a thin layer silica gel plate; eluent: 10% ethyl acetate in hexanes.

Step 2: Preparation of Chiral Benzyl Alkynol (4)

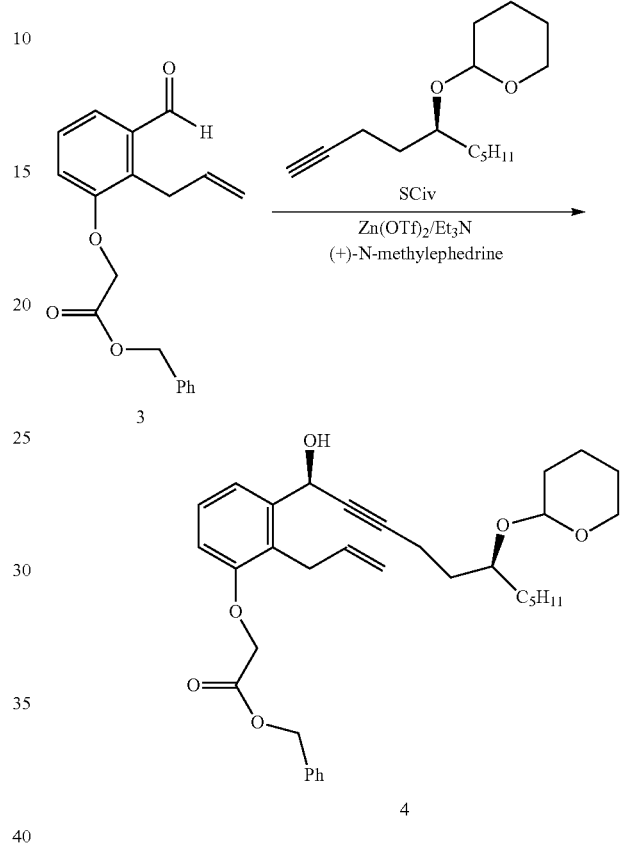

TABLE 8

| Name | MW | Amount | mol |
| --- | --- | --- | --- |
| Aldehyde | 312.00 | 0.250 g | 0.0008 |
| Alkyne side chain (Sciv) | 238.37 | 3.00 g | 0.0025 |
| Zinc triflate | 363.51 | 1.20 g | 0.0030 |
| (+)-N-Methylephedrine | 179.26 | 0.460 g | 0.0025 |
| Triethylamine | 101.19 | 0.810 g | 0.0025 |
| Toluene | NA | 10 mL | NA |

Procedure:

A 50-mL, two-necked, round-bottomed flask equipped with a magnetic stirrer and stir bar was charged with zinc triflate (1.20 g, 0.0030 mol) and (+)-N-methylephedrine (0.460 g, 0.0025 mol) in toluene (5 mL). To this mixture triethylamine was added (0.810 g, 0.0025 mol) and this gelatinous mixture was stirred at ambient temperature for 1-2 h. To this mixture was then added a solution of alkyne (3.00 g, 0.0025 mol) in toluene (4 mL), stirred at ambient temperature for 15-30 minutes followed by addition of a solution of aldehyde (0.250 g, 0.0008 mol in 1-2 mL toluene). Progress of the reaction was monitored by TLC (Note 1). After stirring the mixture at room temperature for 2 h, TLC indicated completion of reaction. The reaction mixture was quenched by slow addition of water (10 mL). This was stirred for 5-10 minutes and organic layer containing desired compound was separated. The aqueous layer was extracted with ethyl acetate (10 mL). The combined organic layers were washed with brine (10 mL), dried over anhydrous sodium sulfate, filtered and the filtrate concentrated in vacuo to obtain a crude product. The crude product was purified by column chromatography using 250-400 mesh silica gel. A solvent gradient of ethyl acetate in hexanes (5-20%) was used to elute the product from the column. All fractions containing the desired pure product were combined and concentrated in vacuo to give pure chiral benzyl alkynol (370 mg, 84%). The structure was consistent with spectral data. $^1$H NMR (CDCl$_3$, 300 MHz) δ 0.84 (τ, 3H), 1.24-1.75 (m, 17H), 2.24-2.30 (m, 2H), 3.43-3.47 (m, 1H), 3.65-3.84 (m, 2H), 3.86-3.87 (m, 1H), 4.63-4.67 (m, 3H), 4.95-4.97 (m, 2H), 5.21 (s, 2H), 5.60 (m, 1H), 5.95-6.04 (m, 1H), 6.70 (m, 1H), 7.18-7.36 (m, 8H).

Note 1: Completion of the reaction was monitored by thin layer chromatography (TLC) using a thin layer silica gel plate; eluent: 20% ethyl acetate in hexanes.

Additional Embodiments

1. A method of preparing a compound represented by the following structural formula:

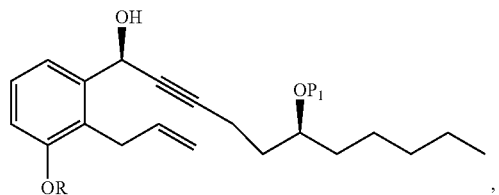

(A)

comprising reacting a compound represented by the following structural formula:

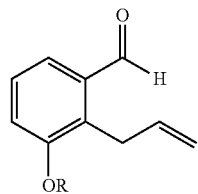

(I)

with a compound represented by the following structural formula:

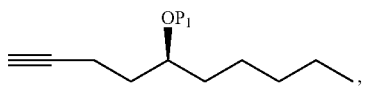

(a)

wherein:
P$_1$ is an alcohol protecting group;
R is —(CH$_2$)$_n$X;
X is H, phenyl, —CN, —OR$_1$ or COOR$_1$;
R$_1$ is an alkyl, THP, TBDMS or a unsubstituted or substituted benzyl group; and
n is 1, 2 or 3.

2. The method of embodiment 1, wherein R is methyl.
3. The method of embodiment 1, wherein R is CH$_2$CO$_2$C$_2$H$_5$.
4. The method of embodiment 1, wherein R is CH$_2$CO$_2$CH$_3$.
5. The method of embodiment 1, wherein R is CH$_2$CO$_2$Bn.
6. The method of embodiment 1, wherein P$_1$ is tetrahydropyranyl (THP).

7. The method of embodiment 1, wherein P$_1$ is tert-butyldimethylsilyl (TBDMS), tertiarybutyldiphenylsilyl (TBDPS), triethylsilyl (TES) or triphenylmethyl (trityl group).
8. The method of embodiment 7, wherein P$_1$ is tert-butyldimethylsilyl (TBDMS).
9. The method of embodiment 1, wherein the reaction is carried out in the presence of chiral inducing agent.
10. The method of embodiment 9, wherein the chiral inducing ligand is (+)-N-methylephederin.
11. The method of embodiment 1, wherein the reaction is carried out in the presence of a base and a zinc reagent.
12. The method of embodiment 11, wherein the base is triethylamine.
13. The method of embodiment 12, wherein the zinc reagent is zinc triflate.
14. A method of preparing a compound represented by the following structural formula:

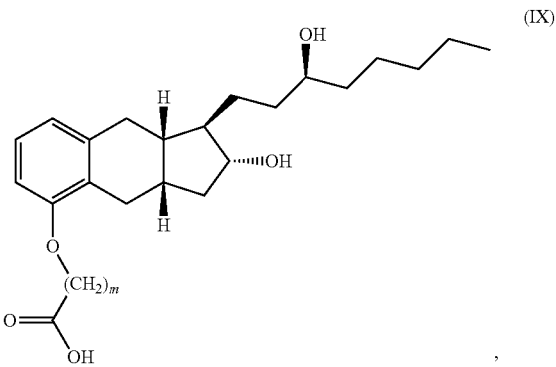

(IX)

or a pharmaceutically acceptable salt thereof, comprising: reacting a compound represented by structural formula (I):

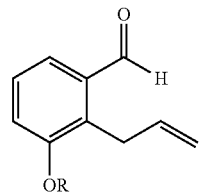

(I)

with a compound represented by structural formula (a):

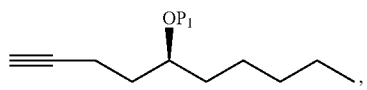

(a)

to form a compound represented by structural formula (A):

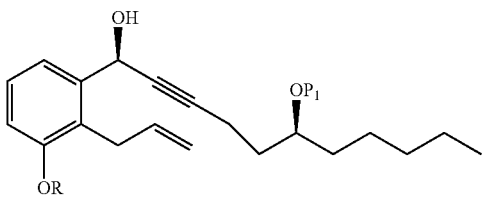

(A)

wherein:
P$_1$ is an alcohol protecting group;
R is —(CH$_2$)$_n$X;
X is H, phenyl, —CN, —OR$_1$ or COOR$_1$;
R$_1$ is an alkyl group, THP, TBDMS or a substituted or unsubstituted benzyl group; and
n is 1, 2 or 3.

15. The method of embodiment 14, further comprising:
(1) reacting the compound of structural formula (A) with an alcohol protecting group to form a compound represented by structural formula (II):

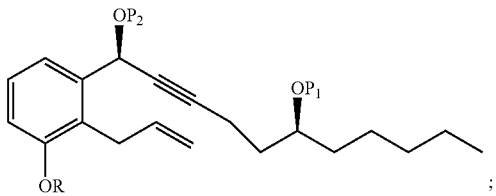

(2) converting the compound of structural formula (II) to a tricyclic compound represented by structural formula (III):

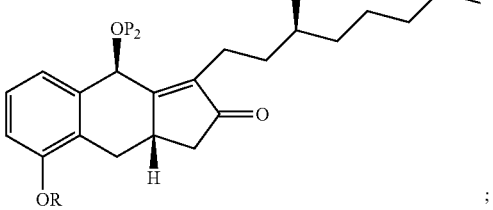

(3) hydrogenating the tricyclic compound of structural formula (III) to form a hydrogenated tricyclic compound represented by structural formula (IV):

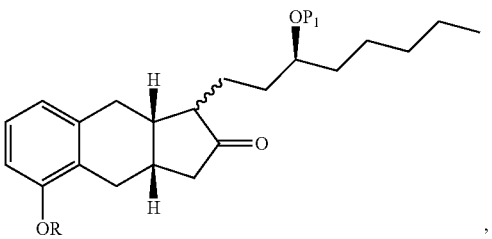

(4) reacting the compound of structural formula (IV) with a reducing agent to form a compound represented by structural formula (V):

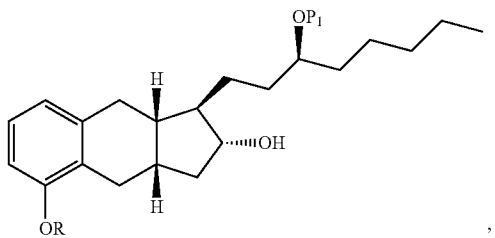

(5) deprotecting the compound of structural formula (V) to form a compound represented by structural formula (VI):

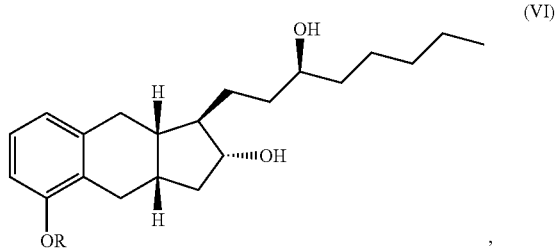

(6) converting the compound represented by structural formula (VI) to a compound represented by structural formula (VII):

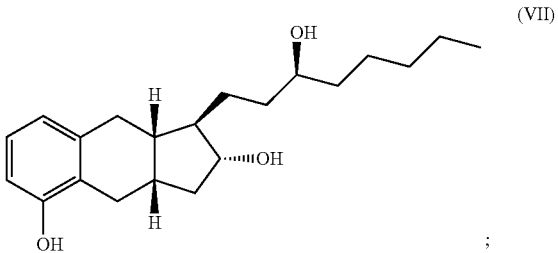 [SMILES: CCCCC[C@H](O)CC[C@@H]1[C@H]2Cc3cccc(O)c3C[C@H]2C[C@H]1O]

(7) reacting the compound represented by structural formula (VII) with $X_1(CH_2)_m CN$ to form a compound represented by structural formula (VIII):

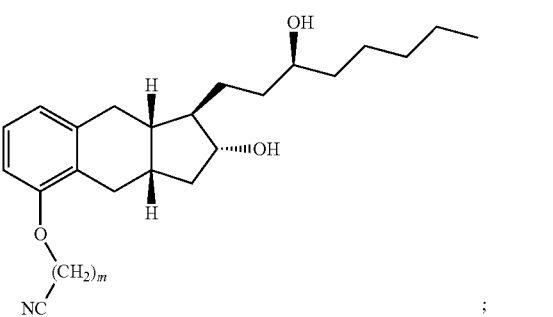

and (8) hydrolyzing the compound of Structural Formula (VIII) to form the compound represented by Structural Formula (IX), wherein:
$P_2$ is an alcohol protecting group;
m is 1, 2 or 3; and
$X_1$ is a leaving group.

16. The method of embodiment 14, wherein R is methyl.
17. The method of embodiment 14, wherein R is $CH_2CO_2C_2H_5$.
18. The method of embodiment 14, wherein $P_1$ is tetrahydrofuranyl (THP).
19. The method of embodiment 14, wherein the compound of structural formula (IX) is tresprostinil represented by the following structural formula:

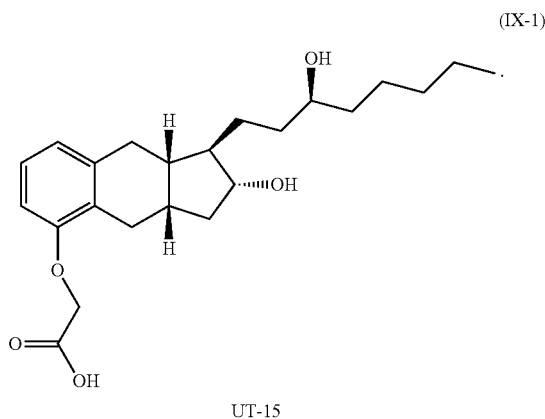 [SMILES: CCCCC[C@H](O)CC[C@@H]1[C@H]2Cc3cccc(OCC(=O)O)c3C[C@H]2C[C@H]1O ; "." ; "UT-15"]

UT-15

20. The method of embodiment 14, wherein the reaction of the compound of structural formula (I) and the compound of structural formula (a) is carried out in the presence of a chiral inducing agent.
21. The method of embodiment 20, wherein the chiral inducing agent is (+)-N-methylephederin.
22. The method of embodiment 20, wherein the reaction is carried out in the presence of a base and a zinc reagent.
23. The method of embodiment 22, wherein the base is triethylamine.
24. The method of embodiment 22, wherein the zinc reagent is zinc triflate.
25. The method of embodiment 15, wherein $P_2$ is tert-butyldimethylsilyl (TBDMS).
26. The method of embodiment 15, wherein for step (2), the compound of structural formula (II) is converted to the compound of structural formula (III) through a cobalt-mediated cyclization reaction.
27. The method of embodiment 26, wherein the cobalt-mediated cyclization reaction is carried out in the presence of $Co_2(CO)_8$.
28. The method of embodiment 15, wherein the hydrogenation reaction of step (3) is carried out in the presence of a base.
29. The method of embodiment 28, wherein the base is $K_2CO_3$.
30. The method of embodiment 15, wherein the reducing agent in step (4) is $NaBH_4$.
31. The method of embodiment 15, wherein for step (5), the compound of structural formula (V) is deprotected in the presence of an acid.
32. The method of embodiment 31, wherein the acid is TsOH.
33. The method of embodiment 15, wherein for step (6), the compound of structural formula (VI) is reacted with nBuLi and $Ph_2PH$.
34. The method of embodiment 15, wherein for step (7), $X_1$ is —Cl.
35. The method of embodiment 15, wherein for step (8), the compound of structural formula (VIII) is hydrolyzed in the presence of a base.
36. The method of embodiment 35, wherein the base is NaOH.
37. The method of embodiment 15, wherein the compound produced by the method is a sodium salt or a diethanolamine salt of treprostinil.
38. The method of embodiment 15, wherein R is $(CH_2)_m CO_2R_1$, wherein $R_1$ is an alkyl or a substituted or unsubstituted benzyl group.
39. The method embodiment 38, further comprising:
(a) reacting the compound of structural formula (A) with a second alcohol protecting group to form a compound represented by structural formula (4):

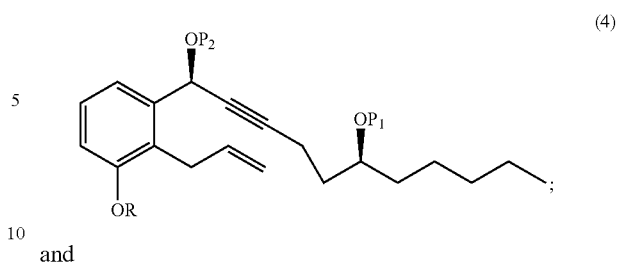

and
(b) converting the compound of structural formula (4) to a tricyclic compound represented by structural formula (5):

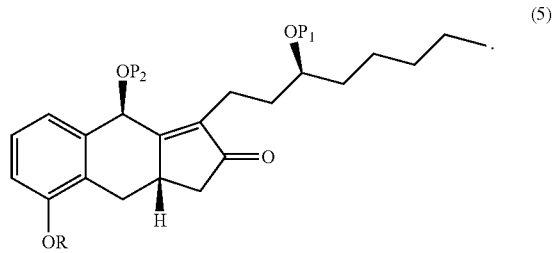

40. The method of embodiment 39, wherein $P_2$ is tert-butyldimethylsilyl (TBDMS), tertiarybutyldiphenylsilyl (TBDPS), triethylsilyl (TES) or triphenylmethyl (trityl group).
41. The method of embodiment 40, wherein $P_2$ is tert-butyldimethylsilyl (TBDMS).
42. The method of embodiment 39, wherein $P_1$ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).
43. The method of embodiment 42, wherein $P_1$ is THP.
44. The method of embodiment 39, wherein m is 1.
45. The method of embodiment 39, wherein for the converting step (b), the compound of structural formula (4) is converted to the compound of structural formula (5) through a cobalt-mediated cyclization reaction.
46. The method of embodiment 45, wherein the cobalt-mediated cyclization reaction is carried out in the presence of $Co_2(CO)_8$.
47. The method of embodiment 39, wherein $R_1$ is an alkyl group and wherein the method further comprises:
(c) hydrogenating the tricyclic compound of structural formula (5) to form a hydrogenated tricyclic compound represented by structural formula (6):

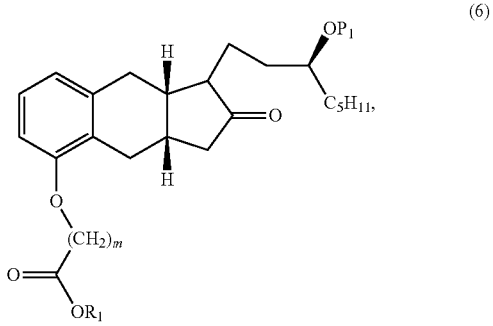

and
(d) converting the hydrogenated tricyclic compound represented by structural formula (6) to a compound represented by structural formula (IX):

(IX)

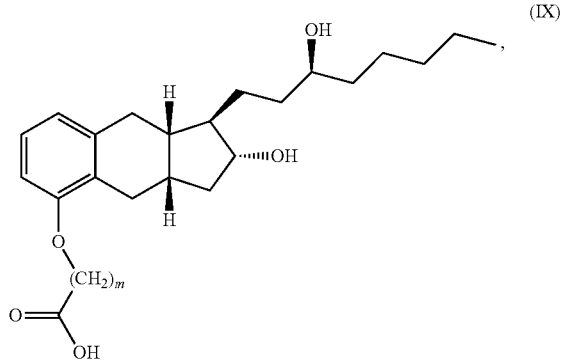

wherein said converting (d) accomplishes cleaving of the protective group $P_1$ and ester hydrolysis of R in a single pot.

48. The method of embodiment 47, wherein the hydrogenation reaction of step (c) is carried out in the presence of a base.
49. The method of embodiment 48, wherein the base is $K_2CO_3$.
50. The method of embodiment 47, wherein $R_1$ is straight or branched C1-5 alkyl.
51. The method of embodiment 50, wherein $R_1$ is methyl.
52. The method of embodiment 39, wherein $R_1$ is a substituted or unsubstituted benzyl group and wherein the method further comprises:
   (c') hydrogenating the tricyclic compound of structural formula (5) to form a hydrogenated tricyclic compound represented by structural formula (6'):

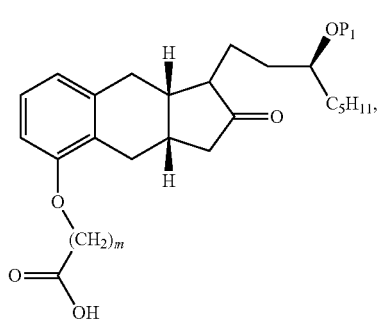
(6')

and
   (d') converting the hydrogenated tricyclic compound represented by structural formula (6') to a compound represented by structural formula (IX):

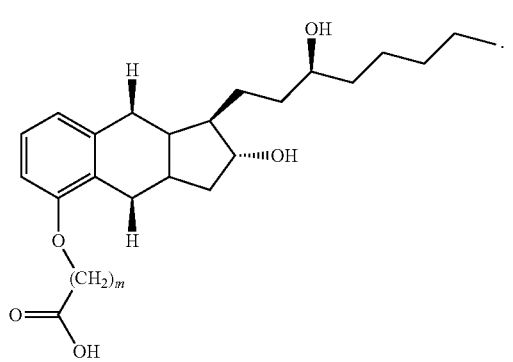
(IX)

53. The method of embodiment 52, wherein the hydrogenation reaction of step (c) is carried out in the presence of a base.

54. The method of embodiment 53, wherein the base is $K_2CO_3$.
55. The method of embodiment 52, wherein $R_1$ is an unsubstituted benzyl group.
56. The method of embodiment 14, further comprising reacting compound represented by formula (1):

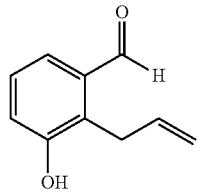
(1)

to form the compound represented by the structural formula

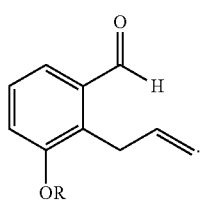
(I)

57. A compound of formula (1):

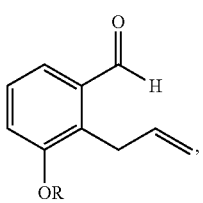
(1)

wherein R is $(CH_2)_mCO_2R_1$, m is 1, 2 or 3, and
   $R_1$ is an alkyl group, THP, TBDMS or a substituted or unsubstituted benzyl group.
58. The compound of embodiment 57, wherein m is 1.
59. The compound of embodiment 57, wherein $R_1$ is straight or branched C1-C5 alkyl.
60. The compound of embodiment 59, where $R_1$ is methyl.
61. The compound of embodiment 57, wherein $R_1$ is unsubstituted benzyl.
62. A compound represented by structural formula (A):

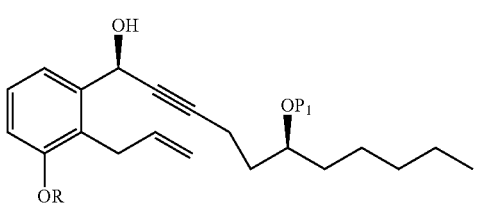
(A)

wherein:
   $P_1$ is an alcohol protecting group;
   wherein R is $(CH_2)_mCO_2R_1$, m is 1, 2 or 3, and
   $R_1$ is an alkyl group or a substituted or unsubstituted benzyl group.

63. The compound of embodiment 62, wherein m is 1.
64. The compound of embodiment 62, wherein $R_1$ is straight or branched C1-C5 alkyl.
65. The compound of embodiment 64, where $R_1$ is methyl.
66. The compound of embodiment 62, wherein $R_1$ is unsubstituted benzyl.
67. The compound of embodiment 62, wherein $P_1$ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).
68. The compound of embodiment 76, wherein $P_1$ is THP.
69. A compound represented by structural formula (4):

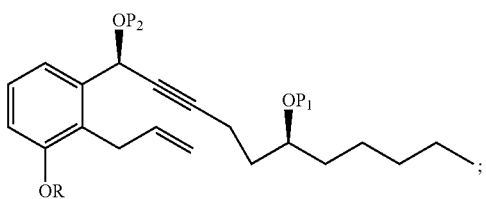

(4)

wherein:
each of $P_1$ and $P_2$ is an alcohol protecting group;
wherein R is $(CH_2)_m CO_2 R_1$, m is 1, 2 or 3, and
$R_1$ is an alkyl group, or a substituted or unsubstituted benzyl group.

70. The compound of embodiment 69, wherein m is 1.
71. The compound of embodiment 69, wherein $R_1$ is straight or branched C1-C5 alkyl.
72. The compound of embodiment 71, where $R_1$ is methyl.
73. The compound of embodiment 62, wherein $R_1$ is unsubstituted benzyl.
74. The compound of embodiment 62, wherein $P_2$ is tert-butyldimethylsilyl (TBDMS), tertiarybutyldiphenylsilyl (TBDPS), triethylsilyl (TES) or triphenylmethyl (trityl group).
75. The compound of embodiment 67, wherein $P_2$ is tert-butyldimethylsilyl (TBDMS).
76. The compound of embodiment 69, wherein $P_1$ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).
77. The compound of embodiment 76, wherein $P_1$ is THP.
78. A compound represented by structural formula (5):

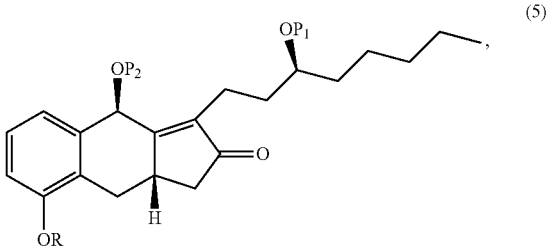

(5)

wherein:
each of $P_1$ and $P_2$ is an alcohol protecting group;
wherein R is $(CH_2)_m CO_2 R_1$, m is 1, 2 or 3, and
$R_1$ is an alkyl group, or a substituted or unsubstituted benzyl group.

79. The compound of embodiment 78, wherein m is 1.
80. The compound of embodiment 78, wherein $R_1$ is straight or branched C1-C5 alkyl.
81. The compound of embodiment 80, where $R_1$ is methyl.
82. The compound of embodiment 78, wherein $R_1$ is unsubstituted benzyl.
83. The compound of embodiment 78, wherein $P_2$ is tert-butyldimethylsilyl (TBDMS), tertiarybutyldiphenylsilyl (TBDPS), triethylsilyl (TES) or triphenylmethyl (trityl group).
84. The compound of embodiment 83, wherein $P_2$ is tert-butyldimethylsilyl (TBDMS).
85. The compound of embodiment 78, wherein $P_1$ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).
86. The compound of embodiment 85, wherein $P_1$ is THP.
87. A compound represented by structural formula (6):

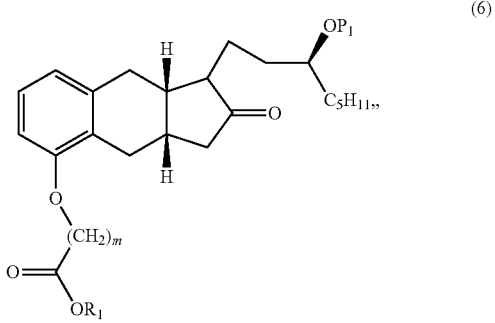

(6)

wherein:
$P_1$ is an alcohol protecting group;
wherein m is 1, 2 or 3, and
$R_1$ is an alkyl group, or hydrogen.

88. The compound of embodiment 87, wherein m is 1.
89. The compound of embodiment 87, wherein $R_1$ is straight or branched C1-C5 alkyl.
90. The compound of embodiment 89, where $R_1$ is methyl.
91. The compound of embodiment 87, wherein $R_1$ is unsubstituted benzyl.
92. The compound of embodiment 87, wherein $P_1$ is tetrahydrofuranyl (THP), benzyl, 2,4-dinitrobenzyl, methoxymethyl (MOM), tertiarybutyldimethylsilyl (TBDMS), tertiarybutyldiphenylsilyl (TBDPS) or triethylsilyl (TES).
93. The compound of embodiment 92, wherein $P_1$ is THP.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of preparing treprostinil or a pharmaceutically acceptable salt thereof comprising a cyclization reaction in which a compound of the formula:

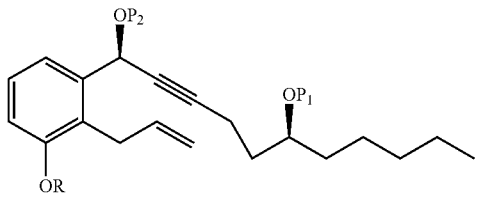

is converted into a compound of the formula:

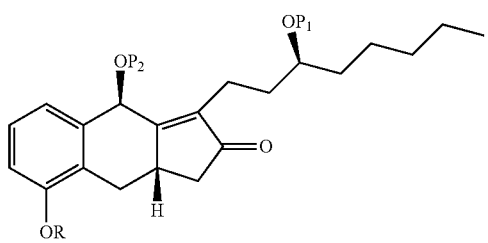

followed by hydrogenation, reaction with a reducing agent, deprotection, and conversion of a triol of formula (VIIa):

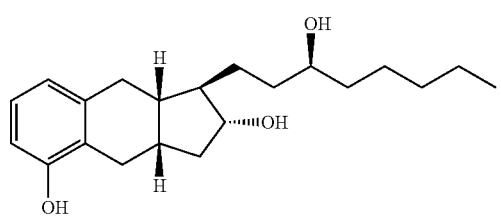 [SMILES: CCCCC[C@H](O)CC[C@@H]1[C@H]2Cc3cccc(O)c3C[C@H]2C[C@H]1O]

into treprostinil or a pharmaceutically acceptable salt thereof, wherein, in each of the above formulas, $P_1$ and $P_2$ are each an independently selected alcohol protecting group;
R is $-(CH_2)_nX$;
n is 0, 1, 2, or 3; and
X is phenyl substituted with one or more substituents independently selected from the group consisting of $-NO_2$, $-CN$, halogen, (C1-C3)alkyl, halo(C1-C3)alkyl, (C1-C3)alkoxy and halo(C1-C3)alkoxy.

2. The method of claim 1, wherein $P_2$ is TBDMS.

3. The method of claim 1, wherein X is phenyl substituted with (C1-C3)alkoxy.

4. The method of claim 1, wherein $Co_2(CO)_8$ is added during the cyclization reaction.

5. The method of claim 4, wherein the cyclization reaction is carried out in a chlorinated solvent.

6. The method of claim 1, wherein the cyclization reaction is carried out in a chlorinated solvent.

7. The method of claim 1, wherein conversion of a triol of formula (VIIa):

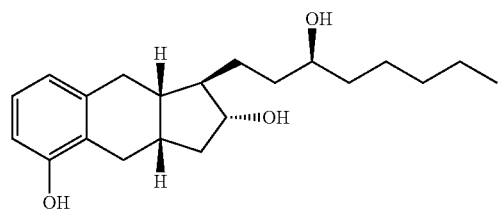 [SMILES: CCCCC[C@H](O)CC[C@@H]1[C@H]2Cc3cccc(O)c3C[C@H]2C[C@H]1O]

into treprostinil or a pharmaceutically acceptable salt thereof is accomplished by reacting the compound represented by structural formula (VIIa) with $X_1(CH_2)_mCN$ to form a compound represented by structural formula (VIII):

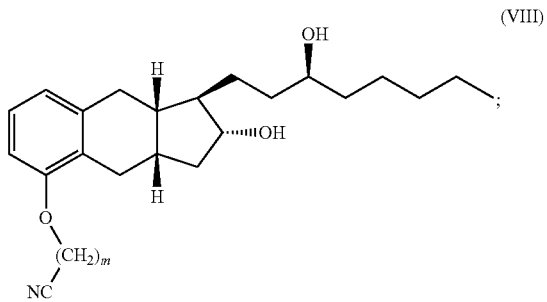

and
hydrolyzing the compound of Structural Formula (V) form treprostinil wherein in is 1 and $X_1$ is a leaving group.

8. The method of claim 1, further comprising, prior to the cyclization reaction, reacting an aldehyde compound represented by structural formula (I):

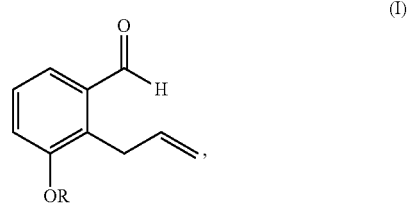

with an alkyne compound represented by structural formula (a):

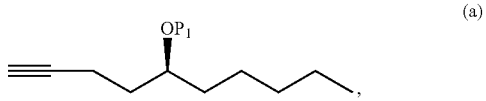

9. The method of claim 8, wherein n is 1.

* * * * *